(12) United States Patent
Sherashova

(10) Patent No.: US 8,452,612 B2
(45) Date of Patent: May 28, 2013

(54) METHOD FOR EVALUATING AND PROGNOSTICATING THE DAILY EMOTIVE BEHAVIOR STATES AND PSYCHOPHYSIOLOGICAL ACTIVITY OF A PERSON ACCORDING TO THE MEASURES OF NIGHT HYPERSYMPATHICOTONIA SYNDROME

(76) Inventor: Nadezhda Viktorovna Sherashova, Moscow (RU)

( * ) Notice: Subject to any disclaimer, the term of this patent is extended or adjusted under 35 U.S.C. 154(b) by 179 days.

(21) Appl. No.: 12/808,324
(22) PCT Filed: Dec. 26, 2008
(86) PCT No.: PCT/RU2008/000804
§ 371 (c)(1), (2), (4) Date: Jun. 15, 2010
(87) PCT Pub. No.: WO2009/084983
PCT Pub. Date: Jul. 9, 2009

(65) Prior Publication Data
US 2010/0280850 A1    Nov. 4, 2010

(30) Foreign Application Priority Data
Dec. 29, 2007 (RU) .................................. 2007148808

(51) Int. Cl.
  *G06Q 10/00* (2012.01)
  *G06Q 50/00* (2012.01)
(52) U.S. Cl.
  USPC .................................. 705/2; 705/3; 600/300
(58) Field of Classification Search
  USPC .......................................... 705/2–3; 600/300
  See application file for complete search history.

(56) References Cited

U.S. PATENT DOCUMENTS
2007/0032733 A1* 2/2007 Burton .......................... 600/509

OTHER PUBLICATIONS

Sorokin et al., Occupational stress as a factor of left ventricular myocardial remodeling in people with normal arterial pressure, 2007, Klin Med (Mosk), abstract.*

(Continued)

*Primary Examiner* — Luke Gilligan
(74) *Attorney, Agent, or Firm* — Notaro, Michalos & Zaccaria P.C.

(57) ABSTRACT

The invention relates to the field of identifying the results of medical measurements. The use thereof ensures the technical result in the form of a possibility for estimating confidently and prognosticating reliably the emotional-behavioral states and psychophysiological functioning of a human by means of data obtained as a result of studying the cardiac rhythm thereof. This result is achieved owing to the method including step of: a) performing an intraday monitoring of the patient's ECG; b) storing the data of this monitoring in the computer memory; c) carrying out a computer processing of the data stored in the step b) for constructing, in accordance with those data, an intervalogram of the patient's cardiac rhythm variability per 24-hour period; d) determining, in accordance with the intervalogram constructed in the step c), those spans corresponding to the nighttime and having at least the predetermined length, where the cardiac rhythm variability is reduced in comparison with the average daily characteristics at the intervalogram spans having the same length and corresponding to the daytime, herewith said reduction of the cardiac rhythm variability shows that the given patient has a night hypersympathicotonia syndrome; e) comparing the differences determined in the step d) with the values from the preformed correspondence set stored in the computer memory, thus defining a degree of manifestation of the predefined indices of the night hypersympathicotonia syndrome; and f) performing, on the basis of the comparison made in the step e), predictive estimations of the human day emotional-behavioral states and psychophysiological functioning.

9 Claims, 15 Drawing Sheets

OTHER PUBLICATIONS

V. Sherashov, False signs of ventricular preexitation syndrome in the liquidators of consequences of a Chernobly nuclear disaster with the symptoms of autonomic nervous dysfunction on hypersympathetic type, Oct. 15, 2001, PACE, Sep. 2001; 24(9, Pt II): S39); (Application p. 4) Open presentation on VII APSPE China, Beijing.

V. S. Sherashov, et al , Clinical and instrumental grounds of the specificity of the ANDS (Autonomic Nervous Dysfunction on hyperSympathetic type) syndrome or vegetative dysfunction on hyperSympathetic type among the liquidators of the consequences of the Chernobyl nuclear disaster in the distant period Journ. Almanac of Clinical Medicine 2006 vol. X pp. 196-201, (Application pp. 4-5) Moscow.

A. Dabrovsky, et al, Diurnal ECG monitoring [in Russian], Medpractic, 1998, pp. 119-127. (Application p. 5) Moscow.

R.M. Baevsky, Estimating the organism functional state based on the mathematical analysis of cardiac rhythm, Academy of Sciences of the USSR, Far Eastern Branch, 1987; (Application pp. 7-8).

R.M. Baevsky, Prognosticating the states on the brink of norm and pathology, Medicine, 1979, pp. 30-45; (Application p. 8) Moscow.

R.M. Baevsky, et al, Medico-biologic aspects of developing the hardware-software means for mathermatical analysis of the cardiac rhythm, Russian medico-biological Bulletin, 1996 (1-2): 104-13; (Application p. 8).

R.M. Baevsky, et al, Estimating the organism adaptive capabilitles and the disease development risk, Medicine, 1997, 236 p.; (Application p. 8) Moscow.

R.M. Baevsky, et al, Analyzing the cardiac rhythm variability when using various electrocardiographic systems (Methodic recommendations), Bulletin of Arhythmology, 2001, (24): 65-86) (Application p. 8).

C.E. Izard, Technique "Differential scales of emotions"("Human emotions", 1980 (Application p. 11), Moscow.

E.S. Romanova, et al, Technique "Mechanisms of psychological protection of the personality"(Mechanisms of psychological protection. Genesis. Functioning. Diagnostic), 1996, 144, (Application p. 12).

E.S. Romanova, et al., Technique of the multi-factor study of the personality by R.B. Cattell (16 PF). (Psychodiagnostic Study guide, 2005, 400). (Application p. 12) St. Petersburg.

* cited by examiner

METHOD FOR EVALUATING AND PROGNOSTICATING THE DAILY EMOTIVE BEHAVIOR STATES AND PSYCHOPHYSIOLOGICAL ACTIVITY OF A PERSON ACCORDING TO THE MEASURES OF NIGHT HYPERSYMPATHICOTONIA SYNDROME

FIELD OF THE INVENTION

The present invention relates to the field of identifying the results of medical measurements and particularly to the method for estimating and prognosticating human day emotional-behavioral states and psychophysiological functioning by indices of the night hypersympathicotonia syndrome.

BACKGROUND OF THE INVENTION

At present, known are various methods for estimating and prognosticating the human functioning by indices of such physiological function as the cardiac rhythm. Such methods are disclosed, for example, in USSR Author's certificate No. 1814875 (publ. 1993.05.15), and in the Russian Patents Nos. 2028078 (publ. 1995.02.09), 2091057 (publ. 1993.09.27), 2099009 (publ. 1997.12.20), 2126649 (publ. 1999.92.27), 2191539 (publ. 2002.10.27), 2240031 (publ. 2004.11.20), 2252692 (publ. 2005.05.27), 2289301 (publ. 2006.12.20), 2297790 (publ. 2007.04.27). In some of these methods, some other physiological functions (pneusis, brain activity, etc.) are analyzed along with the cardiac rhythm.

The Russian Patent No. 2246251 (publ. 2005.02.20) and the Russian Utility Patent No. 45078 (publ. 2005.04.27) disclose the methods for estimating the human psychophysiological state by the cardiac rhythm, in which methods the cardiac rhythm data is subjected to the frequency analysis in order for the data could be later obtained on whether an individual is under stress.

The Russian Patent No. 2312583 (publ. 2007.12.20) discloses the method for determining the rehabilitation actions onto the psychophysiological state of patients in a sanatorium, where the psychophysiological state of the patient is estimated by testing, and the arterial blood pressure is measured herewith.

All the noted documents (except for the last one) are focused on the analysis of the patients' electrocardiograms (ECGs), which analysis, however, is carried out fragmentarily and without relation with results of corresponding psychophysiological tests. In the last of the indicated documents, such a relation (the arterial blood pressure) takes place, but is not integrated.

The integrated estimation based on the ECG monitoring is carried out in the method disclosed in the Russian Patent No. 2212184 (publ. 2003.09.20), but there is no step of estimating the psychophysiological state of the patient.

The background has not proposed or anticipated such a technical solution, where the estimation and prognostication were performed, based on the results of the cardiac rhythm analysis, in regard to the human day emotional-behavioral states and psychophysiological functioning.

SUMMARY OF THE INVENTION

Thus, the object of the present invention consists in providing such a method for estimating and prognosticating the human day emotional-behavioral states and psychophysiological functioning by indices of the night hypersympathicotonia syndrome, which method would enable—as the technical result—the skilled person to estimate confidently and to prognosticate reliably the emotion-behavioral states and psychophysiological functioning of the individual on the basis obtained as a result of examining his/her cardiac rhythm.

In order for solving this problem and achieving said technical result, the present invention provides a method for estimating and prognosticating human day emotional-behavioral states and psychophysiological functioning by indices of the night hypersympathicotonia syndrome, which method comprising steps of: a) performing a 24 hours monitoring of the patient's ECG; b) storing the data of said monitoring in the computer memory; c) carrying out a computer processing of the data obtained in the step b) for constructing, in accordance with those data, an intervalogram in order for obtaining a standard evaluation of the patient's cardiac rhythm variability per 24-hour period; d) determining, in accordance with the intervalogram constructed in the step c), those time spans corresponding to the nighttime and having at least the predetermined length, where the cardiac rhythm variability is reduced in comparison with the average daily characteristics at the intervalogram spans having the same length and corresponding to the daytime, herewith said reduction of the cardiac rhythm variability shows that the given patient has a night hypersympathicotonia syndrome; e) comparing the differences in values determined in the step d) with the values from the preformed correspondence set stored in the computer memory, thus defining a degree of manifestation of the predefined indices of the night hypersympathicotonia syndrome; and f) performing, on the basis of the comparison made in the step e), predictive estimations of the human day emotional-behavioral states and psychophysiological functioning.

The distinction of the method according to the present invention consists in that, in order for forming the correspondence set mentioned in the step f), carried out in advance for a group of individuals are steps g), h), i), and j) corresponding to said steps a), b), c), and d); k) testing the individuals of said group according to preselected criteria right after the monitoring in the step g); l) correlating the characteristics determined in the step k) for the ECG spans revealed in the step j) for each of the individuals of said group with the corresponding results of the psychological testing of that individual in the step k), whereby forming said correspondence set; m) whereafter storing the formed correspondence set in the computer memory.

In so doing, as the preselected criteria of the psychological testing in the step k), used are techniques selected from a group consisting of: the technique "Differential scales of emotions" by C. E. Izard; the technique "Mechanisms of psychological protection of the personality"; and the technique of the multi-factor study of the personality (Sixteen Personality Factor Questionnaire) by R. B. Cattell (16 PF).

Another distinction of the method according to the present invention consists in that, in performing the standard measure of the cardiac rhythm variability in the steps c) or g), a graph of the cardiac rhythm variability of the given individual (patient) could be plotted.

One more distinction of the method according to the present invention consists in that the correspondence set mentioned in the step e) is formed as a table including a first table for finding the degree of manifestation of said indices of the night hypersympathicotonia syndrome by the differences revealed in the step e), and a second table for mapping the degree of manifestation of said indices of the night hypersympathicotonia syndrome found from the first table with a spectrum of the daytime indices of unfavorable human emotion-behavioral states and psychophysiological functioning.

Finally, one more distinction of the method according to the present invention consists in that the predetermined length mentioned in the steps d) or g) is chosen equal or more than 30 minutes.

No technical solutions have been revealed in the background, which comprise both all set of the essential features of the present invention, and the set of features distinguishing the present invention from the closest analog. Therefore, the present invention could be considered novel and possessing the non-obviousness.

BRIEF DESCRIPTION OF THE DRAWINGS

The invention is explained below in the detailed description of the preferred embodiment with references to the illustrating drawings.

DETAILED DESCRIPTION OF THE PREFERRED EMBODIMENT

Figure 1:
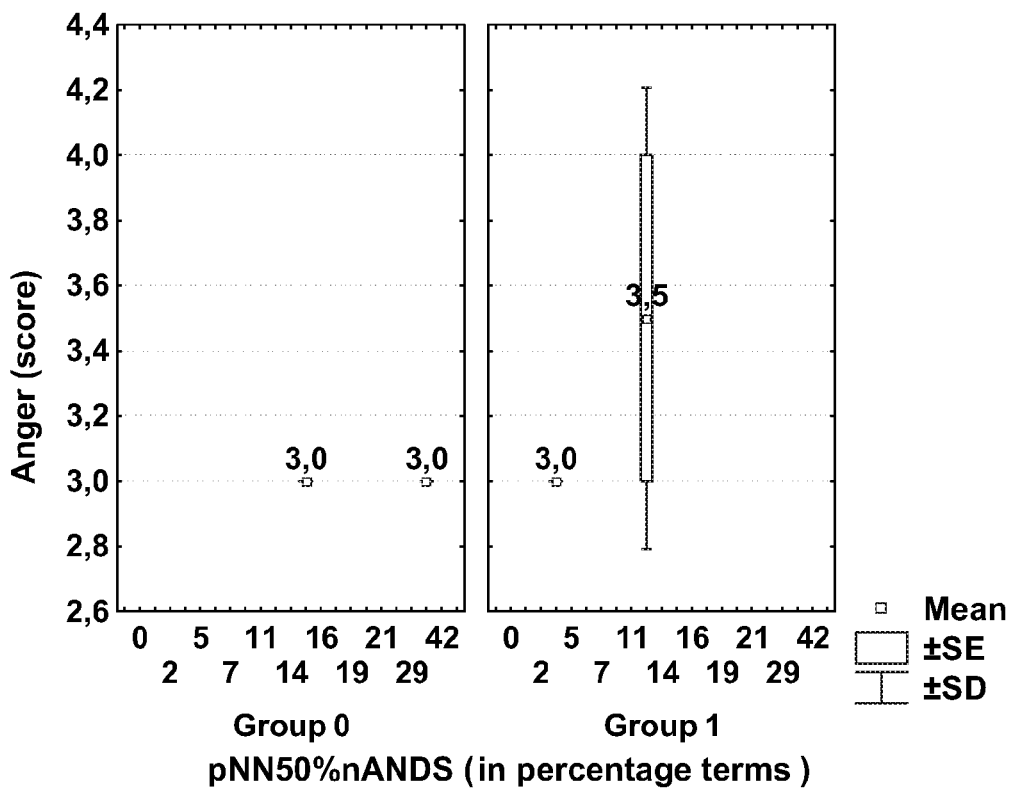
FIGS. 1 to 6 show the diagrams of various daytime indices obtained in accordance with the C. E. Izard technique along with classification by one of the night hypersympathicotonia syndrome indices.

The base of the claimed method is in the dependence found out by the author between the night hypersympathicotonia syndrome and the human emotion-behavioral states and psychophysiological functioning, which appear on the next day.

The night hypersympathicotonia syndrome has been discovered in the 2001 (Sherashov V. False signs of ventricular preexitation syndrome in the liquidators of consequences of a Chernobyl nuclear disaster with the symptoms of autonomic nervous dysfunction on hypersympathetic type. Open presentation on VII APSPE China. Beijing. Oct. 15, 2001. PACE, September 2001; 24(9, Pt II): S39); and, in the Russian-language literature it has been presented in the work: "Clinical and instrumental grounds of the specificity of the ANDS (Autonomic Nervous Dysfunction on hyperSympathetic type) syndrome or vegetative dysfunction on hyperSympathetic type among the liquidators of the consequences of the Chernobyl nuclear disaster in the distant period" by Sherashov V. S., Sherashova N. V., Shalnova S. A. Journ. Almanac of Clinical Medicine. Moscow 2006, Vol. X, pp. 196-201. As has been shown in this study, this syndrome is specific for the liquidators of the consequences of the Chernobyl nuclear disaster, but occurs also in a common population. The main role of this syndrome is in that it is the principal factor defining the growth of the cardiovascular pathology among the liquidators. The syndrome includes a series of symptoms, where could be referenced: occurrence of periods of expressed reduction in the cardiac rhythm variability in the nighttime period—and patients do not notice the sleep disorder; essentially higher rate of ventricular contractions at supraventricular tachyarrhythmia at night owing to the night acceleration of the atrioventricular conduction; occurrence of the false delta-waves in the right chest leads not attributed to the WPW syndrome, also owing to the acceleration of conduction on atrioventricular node.

In order for diagnosticating this night hypersympathicotonia syndrome, it is necessary to carry out the patient's electrocardiogram (ECG) monitoring which is performed, for example, using such a device described in the U.S. Pat. No. 5,275,159 (publ. 1994.01.04), or in the source "Diurnal ECG monitoring" [in Russian] by A. Dabrovsky, B. Dabrovsky, R. Piotrovich.—Moscow, Med-practic, 1998, pp. 119-127. The ECG monitoring, in this context, is referenced to the ECG research performed automatically during a long time period (typically, within 24 hours), when the ECG being registered is processed in the real time together with storing the results of this processing in the computer memory for displaying subsequently these data (onto a screen or paper tape) or for further processing. In such a monitoring, electrocardiographic curves from several (three to five) monitor leads are registered.

The indicated night hypersympathicotonia syndrome is characterized by a series of indices and illustrated, for the purpose of clearness, by examples of intervalograms of some patients without this syndrome and with this syndrome (see. Examples 1 to 6 in FIGS. 22 to 29). These indices are defined by means of analyzing the RR intervals on the ECG, which are, in turn, characterized by the following values:

1) NN is an average RR interval within 24 hours, in ms;

2) SDNN is a standard deviation of NN intervals within 24 hours, in ms;

3) SDANN is a standard deviation of SDNN average values from five-minute segments within 24 hours, in ms;

4) RMSSD is a square root from a sum of squared differences of values of successive pairs of NN intervals within 24 hours, in ms;

5) pNN50% is a percentage of a number of pairs of successive NN intervals differing more than by 50 ms from the total number of successive pairs of NN intervals within 24 hours, in percents;

6) TI(TINN) is a triangular index which is calculated as a distribution density integral (total number of cardiointervals) per the distribution density maximum (the mode amplitude) within 24 hours, in nominal units;

7) HF is a spectrum power in the high-frequency range area of 0.4 to 0.15 Hz (the respiratory waves) calculated during five-minute segments and then averaged within 24 hours;

8) LF is a spectrum power in the low-frequency range area of 0.15 to 0.04 Hz (first order slow waves) calculated during five-minute segments and then averaged within 24 hours;

9) VLF is a spectrum power in the very-low-frequency range area of 0.04 to 0.015 Hz (second order slow waves) within 24 hours;

10) LF/HF is an index of the vagosympathetic interaction, which is calculated as a ratio of the power of the low-frequency spectrum to the high-frequency spectrum of the cardiac rhythm frequency waves within 24 hours;

11) IN is an index of intension of regulatory systems, of a stress index calculated by the formula $AMo/2Mo*M \times DMn$ (where AMo is the mode amplitude, Mo is the mode, $M \times DMn$ is a variation range), by R. M. Baevskiy, within 24 hours (see "Estimating the organism functional state based on the mathematical analysis of the cardiac rhythm" [in Russian] by Baevsky R. M., ed. Academy of Sciences of the USSR, Far Eastern Branch, 1987; "Prognosticating the states on the brink of norm and pathology" [in Russian] by Baevsky R. M., Moscow, Medicine, 1979, pp. 30-45; "Medico-biologic aspects of developing the hardware-software means for mathematical analysis of the cardiac rhythm" [in Russian] by Baevsky R. M., Baevsky A. R., Lapkin M. M., Semenov Yu. N., Shalkin P. V. Russian medico-biological Bulletin, 1996 (1-2): 104-13; "Estimating the organism adaptive capabilities and the disease development risk" [in Russian] by Baevsky R. M., Berseneva A. P. Moscow, Medicine, 1997, 236 p.; "Analyzing the cardiac rhythm variability when using various electrocardiographic systems (Methodic recommendations)" [in Russian] by Baevsky R. M., Ivanov G. G., Chireykin L. V., et al. Bulletin of Arhythmology, 2001, (24): 65-86);

12) NNd is an average RR interval within the day period, in ms;

13) SDNNd is a standard deviation of NN intervals within the day period, in ms;

14) SDANNd is a standard deviation of average SDNN values from five-minute segments within the day period, in ms;

15) RMSSDd is a square root from a sum of squared differences of values of successive pairs of the NN intervals within the day period, in ms;

16) pNN50% d is a percentage of a number of pairs of successive NN intervals differing more than by 50 ms from the total number of successive pairs of NN intervals within the day period, in percents;

17) TI(TINNd) is a triangular index which is calculated as a distribution density integral (total number of cardiointervals) per the distribution density maximum (the mode amplitude) within the day period, in nominal units;

18) HFd is a spectrum power in the high-frequency range area of 0.4 to 0.15 Hz (the respiratory waves) calculated during five-minute segments and then averaged within the day period;

19) LFd is a spectrum power in the low-frequency range area of 0.15 to 0.04 Hz (first order slow waves) calculated during five-minute segments and then averaged within the day period;

20) VLFd is a spectrum power in the very-low-frequency range area of 0.04 to 0.015 Hz (second order slow waves) within the day period;

21) LF/HFd is an index of the vagosympathetic interaction, which is calculated as a ratio of the power of the low-frequency spectrum to the high-frequency spectrum of the cardiac rhythm frequency waves within the day period;

22) INd is an index of intension of regulatory systems, of a stress index calculated by the formula AMo/2Mo*M×DMn (where AMo is the mode amplitude, Mo is the mode, M×DMn is a variation range), by R. M. Baevsky, within the day period;

23) NNn is an average RR interval within the night period, in ms;

24) SDNNn is a standard deviation of NN intervals within the night period, in ms;

25) SDANNn is a standard deviation of average SDNN values from five-minute segments within the night period, in ms;

26) RMSSDn is a square root from a sum of squared differences of values of successive pairs of the NN intervals within the night period, in ms;

27) pNN50% n is a percentage of a number of pairs of successive NN intervals differing more than by 50 ms from the total number of successive pairs of NN intervals within the night period, in percents;

28) TI(TINNn) is a triangular index which is calculated as a distribution density integral (total number of cardiointervals) per the distribution density maximum (the mode amplitude) within the night period, in nominal units;

29) HFn is a spectrum power in the high-frequency range area of 0.4 to 0.15 Hz (the respiratory waves) calculated during five-minute segments and then averaged within the night period;

30) LFn is a spectrum power in the low-frequency range area of 0.15 to 0.04 Hz (first order slow waves) calculated during five-minute segments and then averaged within the night period;

31) VLFn is a spectrum power in the very-low-frequency range area of 0.04 to 0.015 Hz (second order slow waves) within the night period;

32) LF/HFn is an index of the vagosympathetic interaction, which is calculated as a ratio of the power of the low-frequency spectrum to the high-frequency spectrum of the cardiac rhythm frequency waves within the night period;

33) INn is an index of intension of regulatory systems, of a stress index calculated by the formula AMo/2Mo*M×DMn (where AMo is the mode amplitude, Mo is the mode, M×DMn is a variation range), by R. M. Baevsky, within the night period.

Herewith, the indices of the ANDS syndrome are defined as follows:

1) NNnANDS is an average RR interval within the period of the night hypersympathicotonia (syndrome ANDS), in ms;

2) SDNNnANDS is a standard deviation of the NN intervals within the period of the night hypersympathicotonia (syndrome ANDS), in ms;

3) SDANNnANDS is a standard deviation of the average SDNN values from five-minute segments within the period of the night hypersympathicotonia (syndrome ANDS), in ms;

4) RMSSDnANDS is a square root from a sum of squared differences of values of successive pairs of the NN intervals within the night hypersympathicotonia (syndrome ANDS), in ms;

5) pNN50% nANDS is a percentage of a number of pairs of successive NN intervals differing more than by 50 ms from the total number of successive pairs of NN intervals within the night hypersympathicotonia (syndrome ANDS), in ms;

6) TInANDS (TINNnANDS) is a triangular index which is calculated as a distribution density integral (total number of cardiointervals) per the distribution density maximum (the mode amplitude) within the night hypersympathicotonia (syndrome ANDS), in nominal units;

7) HFnANDS is a spectrum power in the high-frequency range area of 0.4 to 0.15 Hz (the respiratory waves) calculated during five-minute segments and then averaged within the night hypersympathicotonia (syndrome ANDS);

8) LFnANDS is a spectrum power in the low-frequency range area of 0.15 to 0.04 Hz (first order slow waves) calculated during five-minute segments and then averaged within the night hypersympathicotonia (syndrome ANDS);

9) VLFnANDS is a spectrum power in the very-low-frequency range area of 0.04 to 0.015 Hz (second order slow waves) within the night hypersympathicotonia (syndrome ANDS);

10) LF/HFnANDS is an index of the vagosympathetic interaction, which is calculated as a ratio of the power of the low-frequency spectrum to the high-frequency spectrum of the cardiac rhythm frequency waves within the night hypersympathicotonia (syndrome ANDS);

11) INnANDS is an index of intension of regulatory systems, of a stress index calculated by the formula AMo/2Mo*M×DMn (where AMo is the mode amplitude, Mo is the mode, M×DMn is a variation range), by R. M. Baevsky, within the night hypersympathicotonia (syndrome ANDS).

The correlation between the dynamic of some of these indices of the ANDS syndrome and the human day emotional-behavioral stares and psychophysiological functioning was discovered during the psychological testing of two groups of individuals, one of which group was the control group. The following three techniques were used as the psychodiagnostics:

technique "Differential scales of emotions" according to C. E. Izard ("Human emotions" [in Russian] by C. E. Izard. Moscow, 1980), technique "Mechanisms of psychological protection of the personality" ("Mechanisms of psychological protection. Genesis. Functioning Diagnostic [in Russian] by Romanova E. S., Grebennikov L. R. Mytishchi, 1996, 144 p.), technique of the multi-factor study of the personality by R. B. Cattell (16 PF). ("Psychodiagnostic. Study guide [in Russian] by Romanova E. S., St. Petersburg, 2005, 400 p.), this techniques including the estimation by primary and secondary factors.

Results of such testing are shown in the Table 1, reflecting the degree of manifestation of the night hypersympathicotonia syndrome in the form of differences in the indices of this syndrome in two groups of individuals: having the verified syndrome ANDS and without signs of this syndrome, and in the Table 2 reflecting the prognostic conformity of the indices of the night hypersympathicotonia syndrome with the human day unfavorable emotional-behavioral states and psychophysiological functioning.

TABLE 1

Results of comparing the indices characterizing the spans of reduced variability in the night period (the night hypersympathicotonia) in the group 1 with the same spans in the control group.

| Indices of the Group 1 vs. Group 0 | Mean value of the Group 1 | Mean value of the Group 0 | t-test | p | Standard deviation | Standard deviation |
|---|---|---|---|---|---|---|
| NNnANDS vs NNnANDS | 910.19 | 951.47 | −0.96 | 0.34560 | 118.07 | 121.62 |
| SDNNnANDS vs SDNNnANDS | 38.37 | 63.80 | −5.53 | 0.00001 | 7.90 | 16.49 |
| SDANNnANDS vs SDANNnANDS | 139.44 | 194.07 | −2.62 | 0.01369 | 56.09 | 59.80 |
| RMSSDnANDS vs RMSSDnANDS | 27.69 | 39.67 | −3.81 | 0.00067 | 6.20 | 10.84 |
| pNN50nANDS vs pNN50nANDS | 8.56 | 20.07 | −3.88 | 0.00055 | 6.11 | 10.05 |
| TInANDS vs TInANDS | 10.50 | 18.27 | −4.41 | 0.00013 | 2.85 | 6.40 |
| VLFnANDS vs VLFnANDS | 888.94 | 2675.93 | −4.35 | 0.00015 | 495.62 | 1562.39 |
| LFnANDS vs LFnANDS | 478.31 | 1266.93 | −4.24 | 0.00021 | 226.29 | 706.84 |
| HFnANDS vs HFnANDS | 276.13 | 740.60 | −4.46 | 0.00011 | 106.32 | 402.40 |
| LF/HFnANDS vs LF/HFnANDS | 1.94 | 1.81 | 0.35 | 0.73224 | 1.29 | 0.71 |
| INnANDS vs INnANDS | 113.13 | 65.27 | 4.83 | 0.00004 | 26.38 | 28.78 |

T-test for independent samples

Group 1: 50 patients having the ANDS syndrome (52.91 ± 10 years);

Group 0: 50 patients without signs of the ANDS syndrome and having the similar nosology (51.0 ± 13 years)

Note:

n is a prefix characterizing the accessory of an index to the night period;

ANDS is a prefix characterizing the accessory to the night hypersympathicotonia syndrome for the group 1 and characterizing the similar changes in the control group (group 0).

TABLE 2

Prognostication correspondence of the night hypersympathicotonia syndrome indices with unfavorable human day emotional-behavioral states and psychophysiological functioning

| Technique | Night hypersympathicotonia index differing significantly the morning characteristics of the emotional-behavioral states in the Group 1 and in the Group 0 (two-factor variation analysis according to Milliken & Johnson, 1992) | Index in the next morning | SS Effect | MS Effect | F | $p_2$ | Fig. No. |
|---|---|---|---|---|---|---|---|
| C. E. Izard | (↓) pNN50%nANDS, $p_1$ < 0.0006 | (↑) Anger | 36.27 | 1.40 | 11.16 | 0.01 | 1 |
| | (↓) RMSSDnANDS, $p_1$ < 0.0007 | (↑) Anger | 36.02 | 1.57 | 14.62 | 0.0006 | 2 |
| | | (↑) Disgust | 105.77 | 4.60 | 32.19 | 0.00005 | 3 |
| | | (↑) Scorn | 42.60 | 1.85 | 17.29 | 0.0003 | 4 |
| | (↓) TInANDS, $p_1$ < 0.00013 | (↓) Joy | 115.34 | 5.49 | 3.03 | 0.04 | 5 |
| | | (↑) Fear | 16.17 | 0.77 | 10.40 | 0.0005 | 6 |
| MPPP | (↓) pNN50%nANDS, $p_1$ < 0.0006 | (↑) Compensation | 79.37 | 3.05 | 24.42 | 0.003 | 7 |
| | | (↑) Extrajection | 194.35 | 7.48 | 5.98 | 0.04 | 8 |
| R. B. Cattell, primary factors | (↓) SDNNnANDS, $p_1$ < 0.00001 | (↓) Factor I | 110.32 | 4.41 | 6.97 | 0.02 | 9 |
| | | (↓) Factor Q4 | 231.61 | 9.26 | 6.46 | 0.02 | 10 |
| | (↓) pNN50%nANDS, $p_1$ < 0.0006 | (↓) Factor I | 112.21 | 4.32 | 6.91 | 0.03 | 11 |
| | | (↓) Factor A | 112.98 | 4.35 | 34.76 | 0.002 | 12 |
| | (↓) TInANDS, $p_1$ < 0.00013 | (↓) Factor A | 104.38 | 4.97 | 4.33 | 0.01 | 13 |
| | | (↓) Factor C | 81.11 | 3.86 | 4.53 | 0.01 | 14 |
| | | (↓) Factor F | 80.74 | 3.84 | 3.84 | 0.02 | 15 |
| | | (↓) Factor I | 104.32 | 4.97 | 4.88 | 0.009 | 16 |
| | (↑) INnANDS, $p_1$ < 0.00004 | (↓) Factor F | 88.74 | 3.41 | 13.65 | 0.01 | 17 |
| | | (↓) Factor Q3 | 151.84 | 5.84 | 7.79 | 0.03 | 18 |

TABLE 2-continued

Prognostication correspondence of the night hypersympathicotonia syndrome indices with unfavorable human day emotional-behavioral states and psychophysiological functioning

| Technique | Night hypersympathicotonia index differing significantly the morning characteristics of the emotional-behavioral states in the Group 1 and in the Group 0 (two-factor variation analysis according to Milliken & Johnson, 1992) | Index in the next morning | SS Effect | MS Effect | F | $p_2$ | Fig. No. |
|---|---|---|---|---|---|---|---|
| R. B. Cattell, second order factors | (↓)RMSSDnANDS, $p_1 < 0.0007$ | (↓) Factor F2 | 72.08 | 3.13 | 3.59 | 0.04 | 19 |
|  | (↓)pNN50%nANDS, $p_1 < 0.0006$ | (↑) Factor F3 | 172.91 | 6.65 | 7.00 | 0.03 | 20 |
|  | (↓)TInANDS, $p_1 < 0.00013$ | (↓) Factor F2 | 70.33 | 3.35 | 3.84 | 0.02 | 21 |

Notes:
n is a prefix of the accessory to the night period;
ANDS is a prefix of the accessory to the verified night hypersympathicotonia syndrome. In the control group without signs of the established night hypersympathicotonia syndrome, "ANDS" signifies that the indices of the similar nighttime spans of reduced cardiac rhythm variability were taken into account, but only those spans that had reliably lesser reduction of the variability in further comparing (Table 1);
SS Effect is the effect of the squared sum (here: intergroup variations);
MS Effect is the effect of the mean value of squares (intragroup variations);
F is the criterion of the value of variation differences;
$p_1$ is the assurance of differences from similar nighttime indices in the control group;
$p_2$ is the assurance of variation intergroup differences of the morning indices of psychological testing, caused by the night hypersympathicotonia;
MPPP is the psychological test "Mechanisms of psychological protection of the personality".

The above two Tables are shown for the illustration purposes only, since the adduced dependences could be quite possible to reduce into one Table, or simply present as a set of respective data stored in the computer memory.

After the dependences illustrated in the Tables 1 and 2 are established, the method of the present invention is carried out as follows.

The ECG monitoring of the selected patient is carried out within 24 hours. The ECG recording taken during this monitoring is stored in the computer memory in the form of digitized samples of the varying cardiac activity potentials from respective lead(s). In principle, such a recording could be used as such without any processing. However, the informativity of such a recording is not too high due to a very great (up to a hundred of thousands) number of the cardiac rhythm frequency at a relatively small span. When extending this recording to the scale used in taking a customary ECG, it is often not physically possible for skilled person to look through such long recording.

Therefore, as well as in order for increasing the accuracy and informativity, the data stored in the computer memory are processed for constructing, in accordance with those data, an intervalogram in order for obtaining a standard measure of the patient's cardiac rhythm variability per 24-hour period. This standard measure is carried out in accordance with the accepted recommendations (see Heart rate variability. Standards of measurement, physiological interpretation, and clinical use. Task Force of The European Society of Cardiology and The North American Society and Electrophysiology. Eur. Heart J. 1996; (17):354-381).

According to the intervalogram constructed in the previous step, the spans having a predetermined length are determined, which spans correspond to the nighttime and at which spans the cardiac rhythm variability is reduced in comparison with the average daily characteristics at the spans of the same intervalogram having the same length and corresponding to the daytime. As is shown in the above document ("Clinical and instrumental grounds of the specificity of the ANDS . . . "), the reduction of the cardiac rhythm variability manifests that the given patient possesses the night hypersympathicotonia syndrome.

The detected differences at a "nighttime" and "daytime" intervalogram spans of the same length are compared with the values from the correspondence set (e.g., in the form of the above Tables 1 and 2) formed in advance and stored in the computer memory. In so doing, a degree of manifestation of the predefined indices of the night hypersympathicotonia syndrome is defined.

After that, based on the thus performed comparison, prognosis estimates of the human day emotional-behavioral states and psychophysiological functioning are performed.

It could be noted here that in compiling the above Tables 1 and 2, carried out are steps of: monitoring the ECG in a group of individual, storing the results of that monitoring, computer processing the stored data along with constructing the intervalograms, and searching the "nighttime" spans distinguished from the corresponding "daytime" spans. Then, after performing, following the step of monitoring and the above psychological testing, correlating the characteristics determined in the respective intervalogram spans for each of the individuals of said group with the corresponding results of the psychological testing of that individual, whereby forming said correspondence set. Thereafter, storing the formed correspondence set in the computer memory.

When performing the above standard evaluation of the patient's cardiac rhythm variability, a graph of the cardiac rhythm variability of the given patient could be plotted. Such a graph could be convenient for operational estimating the probable human day emotional-behavioral states and psychophysiological functioning It could be noted that it is expedient to choose the above intervalogram spans selected for the step of correlating, having a length of not less than 30 minutes.

Refer first to FIGS. 22-29 illustrating the detection of the night hypersympathicotonia syndrome in the following examples.

EXAMPLE 1

Figure 22:
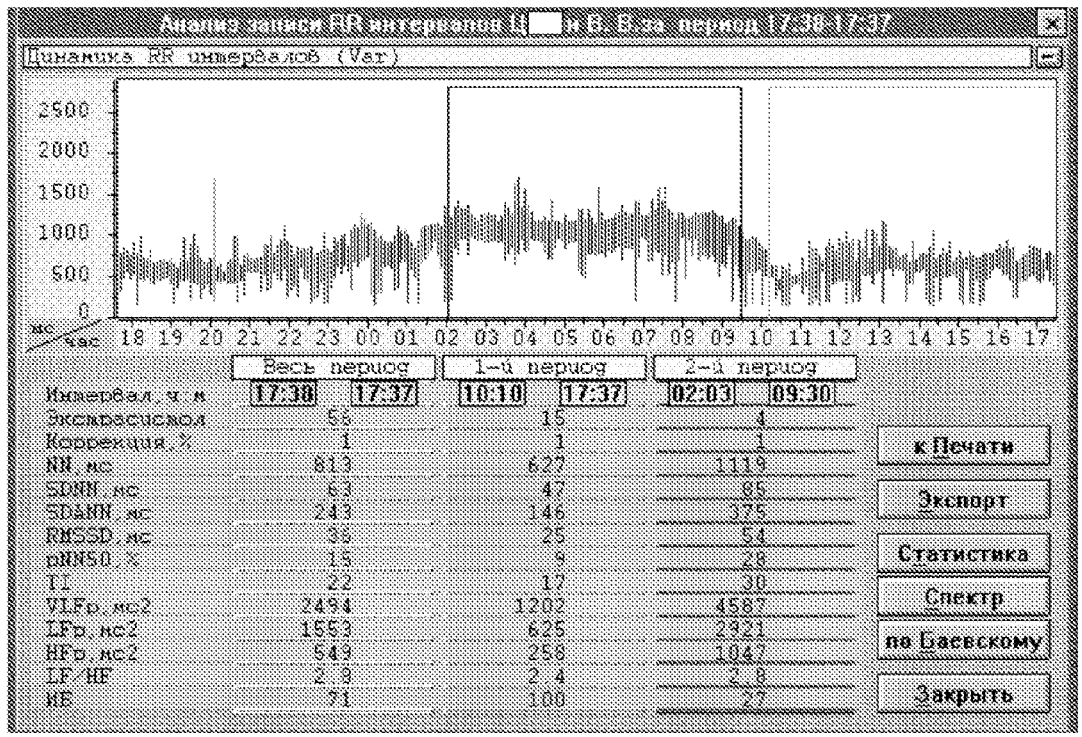
FIGS. 22 to 29 show types of the intervalograms of various individuals as the illustrations.

Patient Ts-n, 51 years old. FIG. 22 shows the intervalogram without signs of the night hypersympathicotonia. The first time period characterizes the rhythm variability during a day wakefulness from 10:10 am to 5:37 pm, the period length is equal to 7 hours 27 minutes. The second period from 2:03 am to 9:30 am having the length similar to the daytime characterizes the sleep period.

The variability indices in the nighttime period exceed the daytime ones, which corresponds for the given individual to the physiological predominance of the night vagotonia, which demonstrates the absence of the night hypersympathicotonia syndrome.

Figure 23:
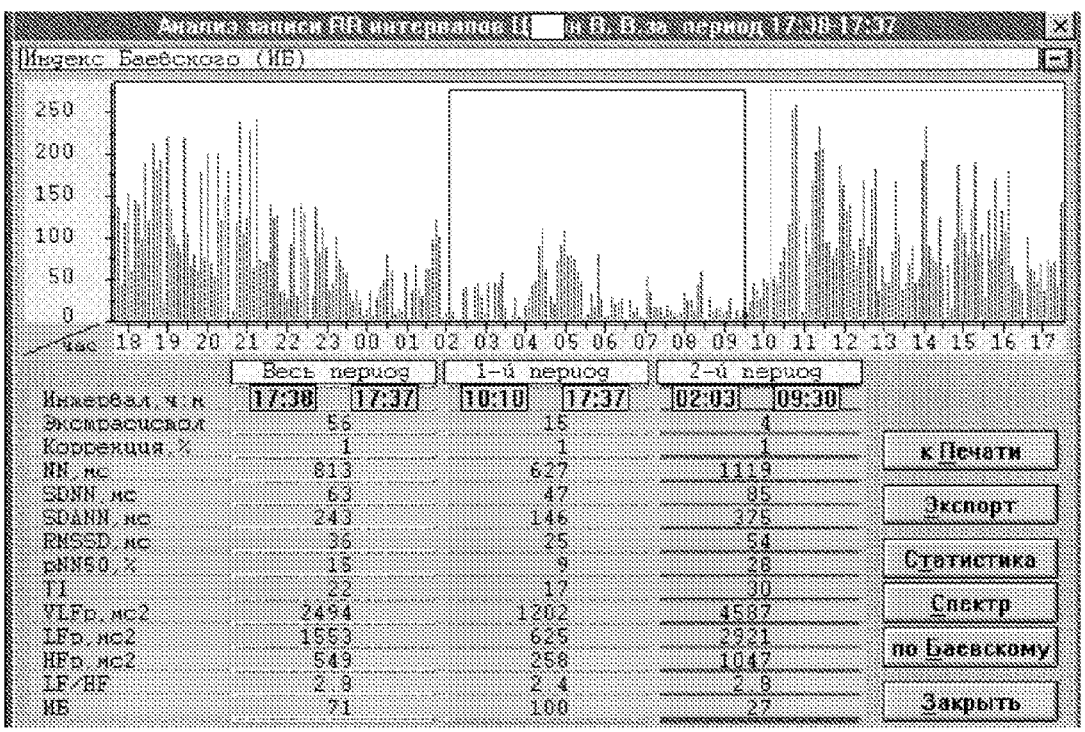

FIG. 23 shows the dynamic of the diurnal value of the index of intension of the vegetative regulation according to R. M. Baevsky (IN), which dynamic confirms the physiological sympathetic activity in the daytime and the absence thereof in the nighttime, which demonstrates the absence of the night hypersympathicotonia syndrome.

EXAMPLE 2

Figure 24:
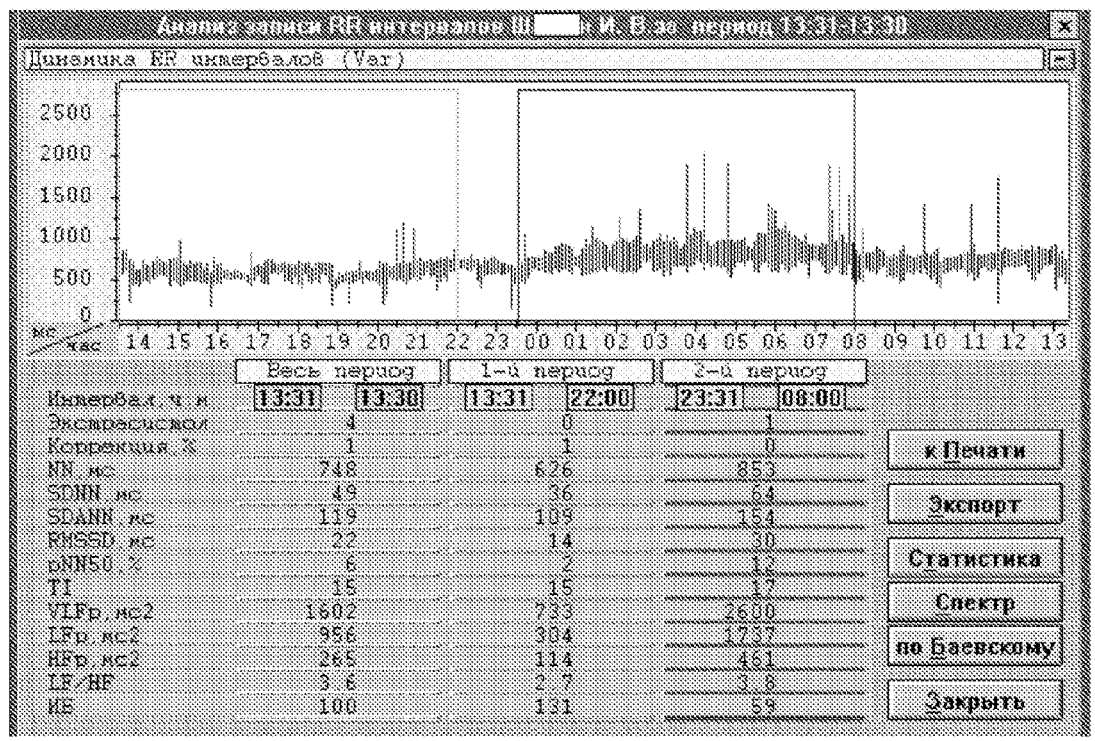

Patient Sh-n, 54 years old. FIG. 24 shows the intervalogram without signs of the night hypersympathicotonia. The first time period characterizes the rhythm variability in the wakefulness period including the day and evening periods from 1:31 pm to 10:00 pm, the period length is equal to 8 hours 29 minutes. The second period from 11:31 pm to 8:00 am having the length similar to the daytime one characterizes the sleep period.

The variability indices in the nighttime period exceed the daytime ones, which corresponds for the given individual to the physiological predominance of the night vagotonia, i.e., the absence of the night hypersympathicotonia syndrome.

EXAMPLE 3

Figure 25:
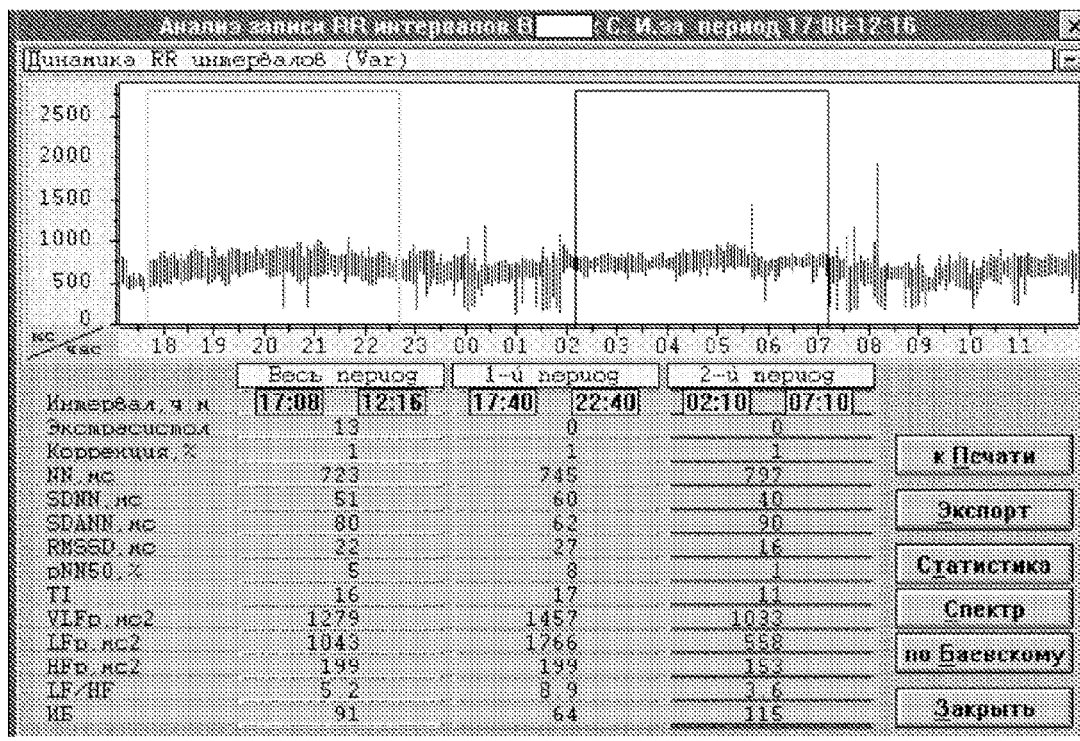

Patient V-k C.I., 50 years old. FIG. 25 shows the intervalogram having signs of the night hypersympathicotonia syndrome. The first time period characterizes the rhythm variability in the wakefulness period including the day and evening periods from 5:40 pm to 10:40 pm, the period length is equal to 5 hours 29 minutes. The second period from 2:10 am to 7:10 am having the length similar with the daytime one characterizes the sleep period.

The variability indices in the nighttime period are lower than the daytime ones, which corresponds for the given individual to significantly greater increase of the activity of the sympathetic part of the nervous system in comparison with the daytime indices thereof.

EXAMPLE 4

Figure 26:
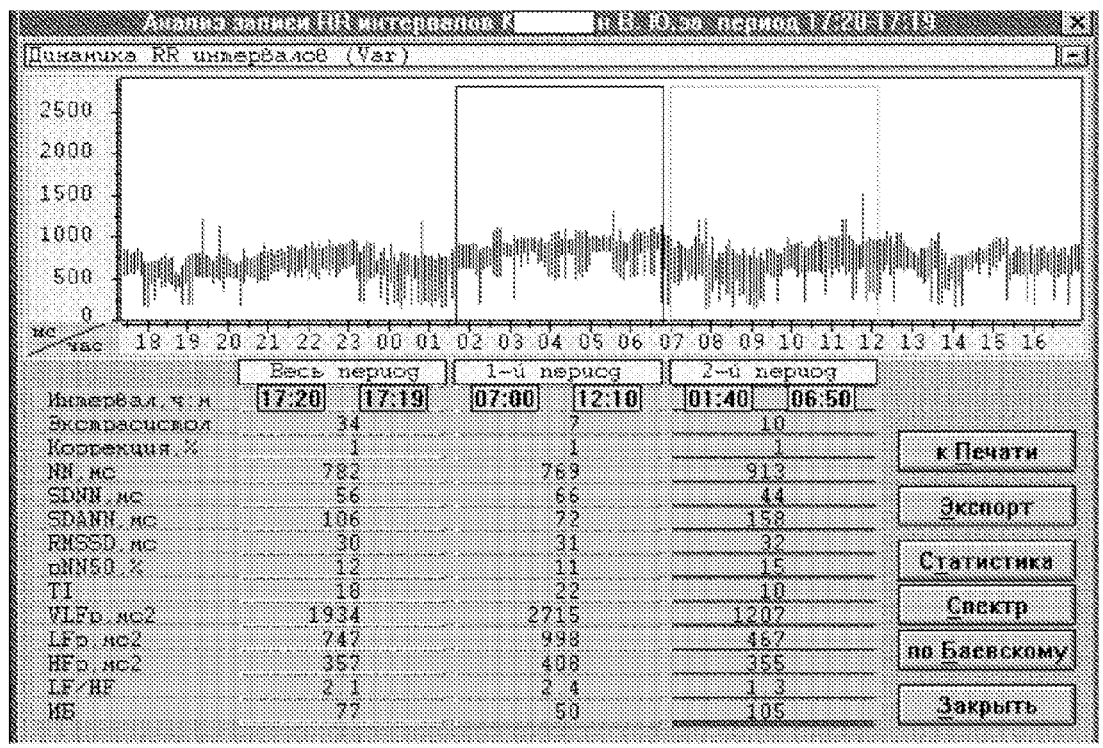
Figure 27:
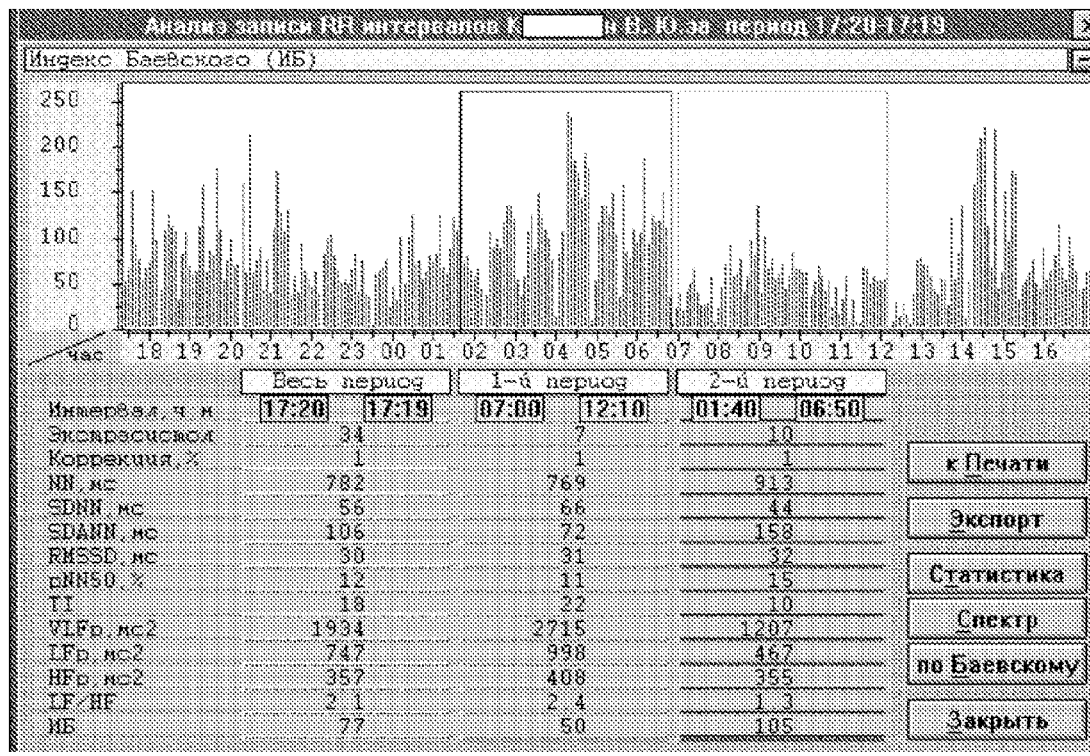

Patient K-n V.Yu., 49 years old. FIG. 26 shows the intervalogram having signs of the night hypersympathicotonia syndrome. The first time period characterizes the rhythm variability in the wakefulness period including the morning period from 7:00 am to 12:10 am, the period length is equal to 5 hours 10 minutes. The second period from 1:40 am to 6:50 am having the length similar with the daytime one characterizes the sleep period.

The variability indices in the nighttime period are lower than the daytime ones, which corresponds for the given individual to significantly greater increase of activity of the sympathetic part of the nervous system in comparison with the daytime indices thereof.

The dynamic of the diurnal value of the index of intension of the vegetative regulation according to R. M. Baevsky (IN) shown in FIG. 27 confirms the more expressed sympathetic activity in the nighttime period during the sleep, which demonstrates the presence of the night hypersympathicotonia syndrome.

EXAMPLE 5

Figure 28:
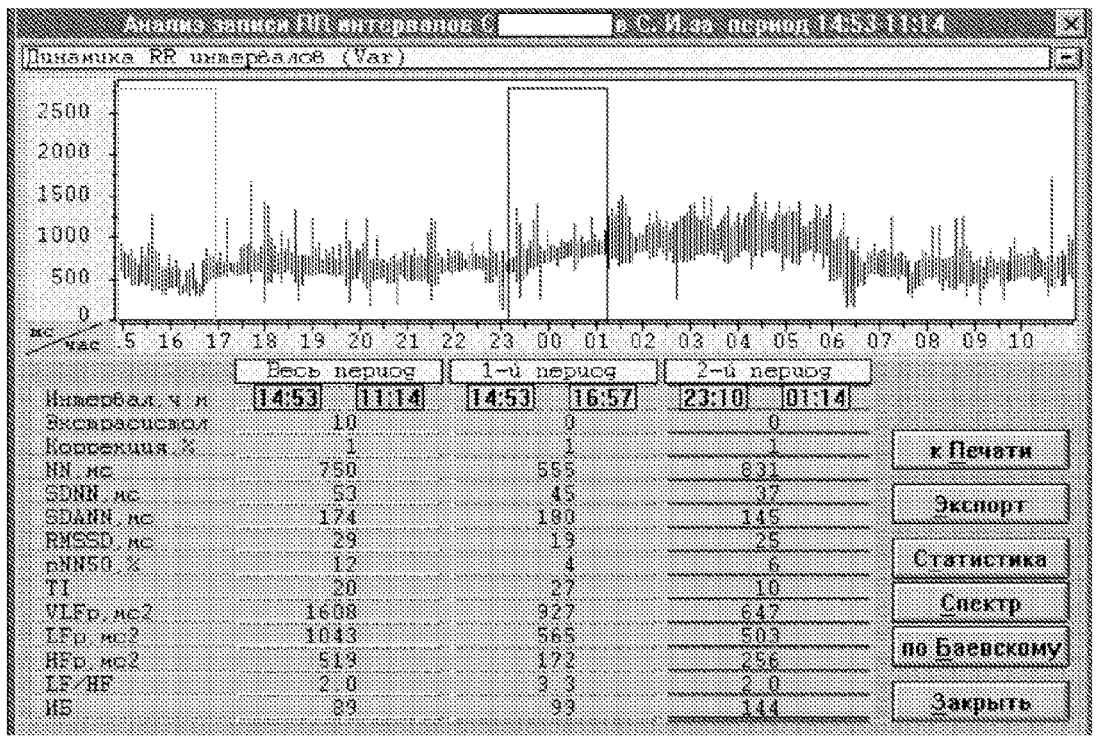

Patient S-v S.I., 45 years old. FIG. 28 shows the intervalogram having signs of the incomplete night hypersympathicotonia syndrome. The first time period characterizes the rhythm variability in the wakefulness period including the day period from 2:53 pm to 4:57 pm, the period length is equal to 2 hours 4 minutes. The second period from 11:10 pm to 1:14 am having the length similar with the daytime one characterizes the first half of the nighttime, where the patient is observed to have in the sleep the signs of the sympathetic activity exceeding the daytime ones, which signifies the presence of the incomplete night hypersympathicotonia syndrome (the variability indices in the nighttime period are lower than the daytime ones, which corresponds for the given patient to the significantly greater increase of activity of the sympathetic part of the nervous system in comparison with the daytime indices thereof).

EXAMPLE 6

Figure 29:
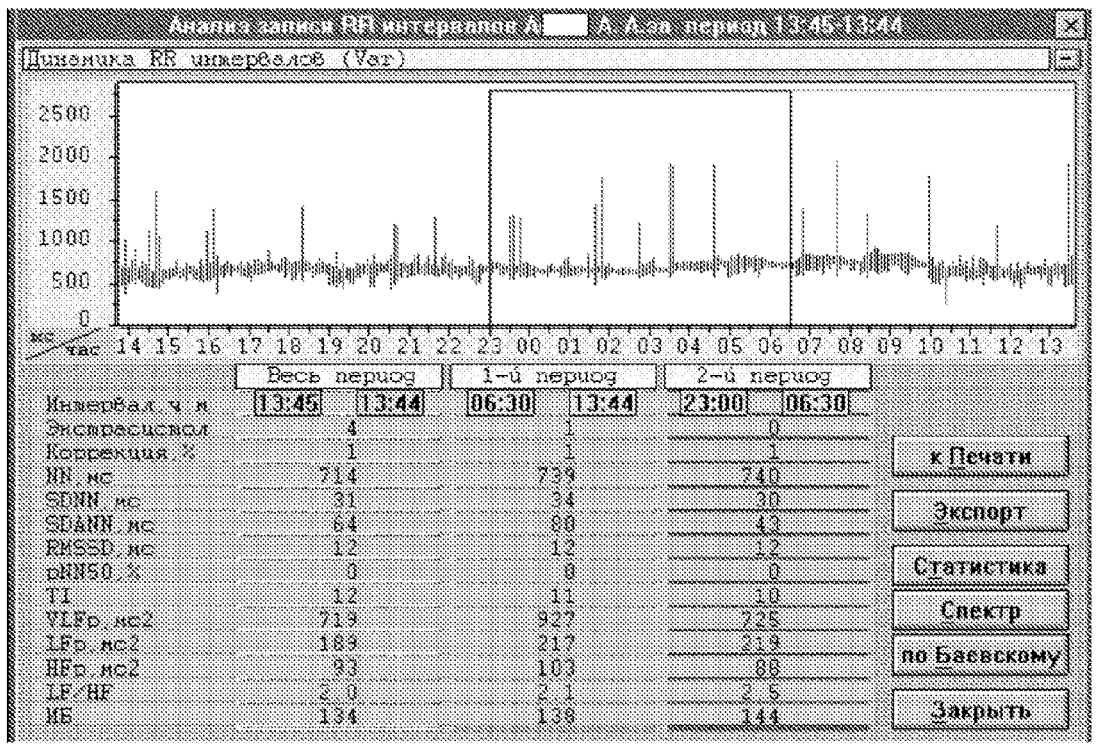

Patient A-v A.A., 42 years old. FIG. 29 shows the intervalogram having tremendous disturbance of the vegetative regulation as a whole within 24 hours and, at the same time, signs of the night hypersympathicotonia syndrome. The first time period characterizes the rhythm variability in the wakefulness period including the morning period from 6:30 am to 1:44 pm, the period length is equal to 7 hours 14 minutes. The second period from 11:00 pm to 6:30 am having the length similar with the daytime one characterizes the sleep period.

The variability indices in the nighttime period are lower than the daytime ones, which corresponds for the given individual to significantly greater increase of activity of the sympathetic part of the nervous system at night in comparison with the morning indices thereof.

Refer now to FIGS. 1-21 which represent the diagrams of various daytime indices obtained in accordance with one or another psychological tests. Explanations of each of those diagrams are given directly in respective drawing. Interpretation of the results shown in those diagrams is given below with references to the above Tables 1 and 2.

As it appears from the Table 2, the statistically significant indices of the night hypersympathicotonia syndrome, which predestinate the morning differences of characteristics in accordance with the C. E. Izard technique in the group 1 (hereinafter, GR. 1) have been the indices pNN50% nANDS, RMSSDnANDS, and TInANDS, where n means the accessory to the nighttime period, and ANDS means the accessory of an index to the night hypersympathicotonia syndrome. The indices pNN50% nANDS and RMSSDnANDS distinguish the characteristics of anger, disgust, scorn, fear. The lower was an index value that signifies intensifying the night sympathetic activity, the higher were values of the characteristics of anger, disgust, scorn, fear in the GR. 1 in the next morning (see FIGS. 1-4). The index TInANDS predestinated the characteristics of joy and fear. The night decrease of this index in the GR. 1 predestined decreasing the joy and increasing the fear on the next day (see FIGS. 5, 6).

Figure 7:
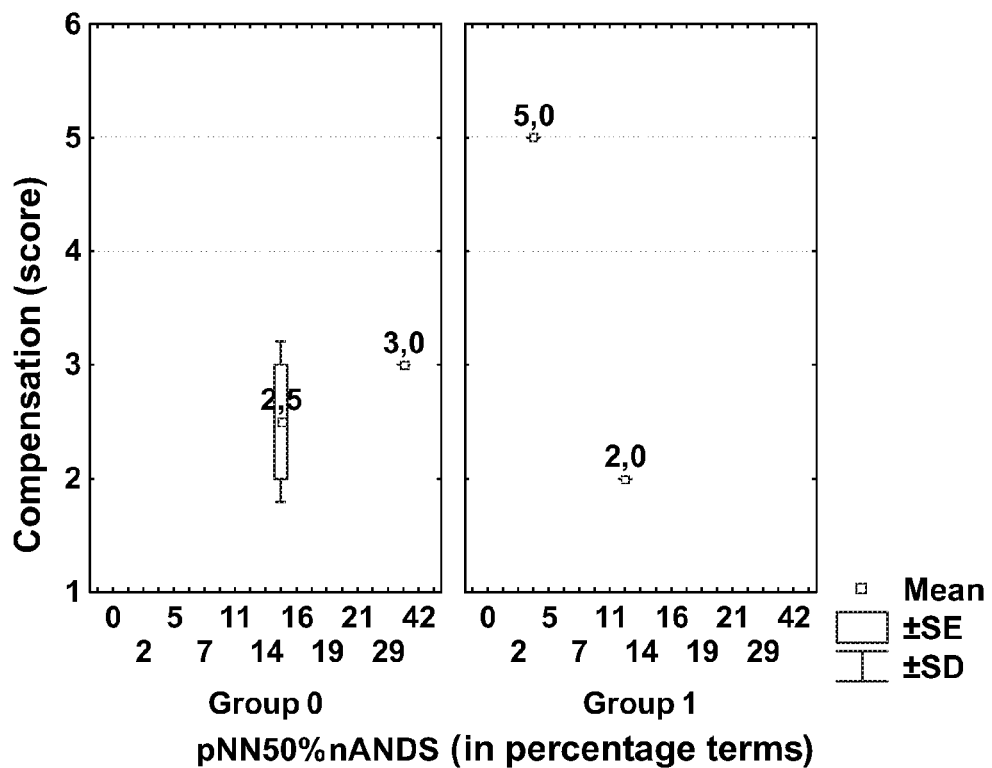
FIGS. 7 and 8 show the diagrams of various daytime indices obtained in accordance with the technique "Mechanisms of psychological protection of the personality" (MPPP) along with classification by one of the night hypersympathicotonia syndrome indices.

The statistically significant index of the night hypersympathicotonia syndrome, that predestined the morning differences of the characteristics in accordance with the technique "Mechanisms of psychological protection of the personality" have been the index pNN50% nANDS. Relative nighttime decrease of this index in the GR. 1 was accompanied with the morning increase of the characteristic "compensation" signifying a relative intensification of such properties as attribution of negative properties to others, modesty, strictness, intolerance to superiory of another person, tendency to envy (FIG. 7). The index pNN50% nANDS predestined also the growth of the characteristic "extrajection" (FIG. 8), which signifies intensifying such properties as latent (concealed) megalomania, identification oneself with the ideal, realization of the inability complex in dreams, overcompensatory desire to prove own significance to everybody.

Figure 9:
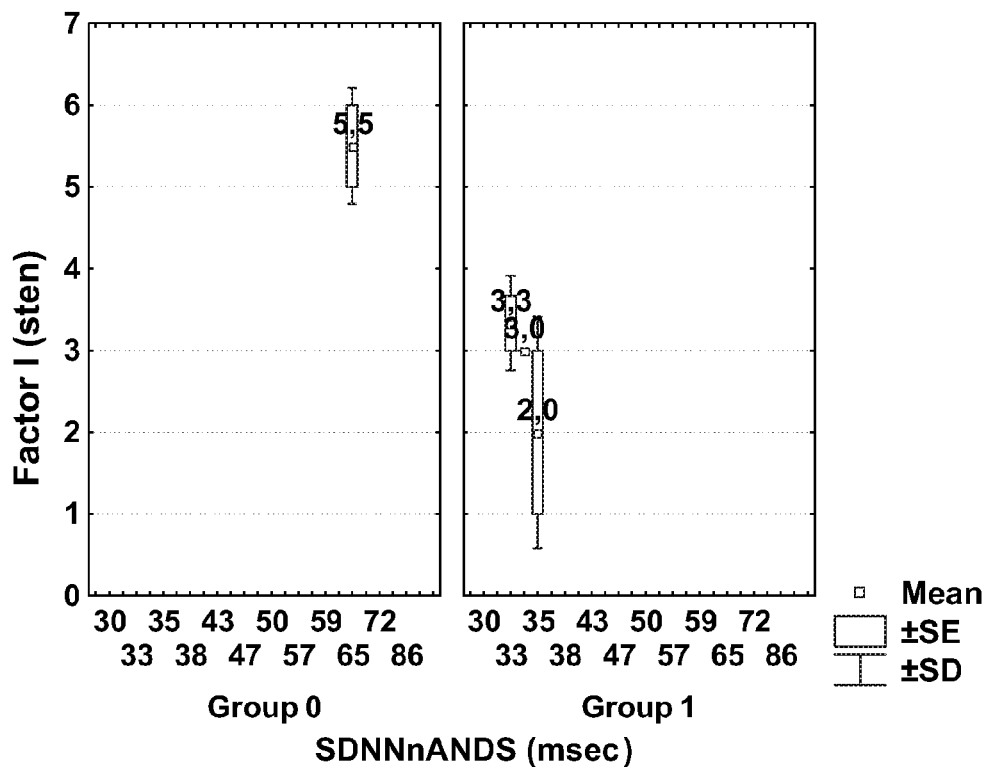
FIGS. 9 to 18 show the diagrams of various daytime indices obtained in accordance with the R. B. Cattell technique along with classification by one of the night hypersympathicotonia syndrome indices.
Figure 10:
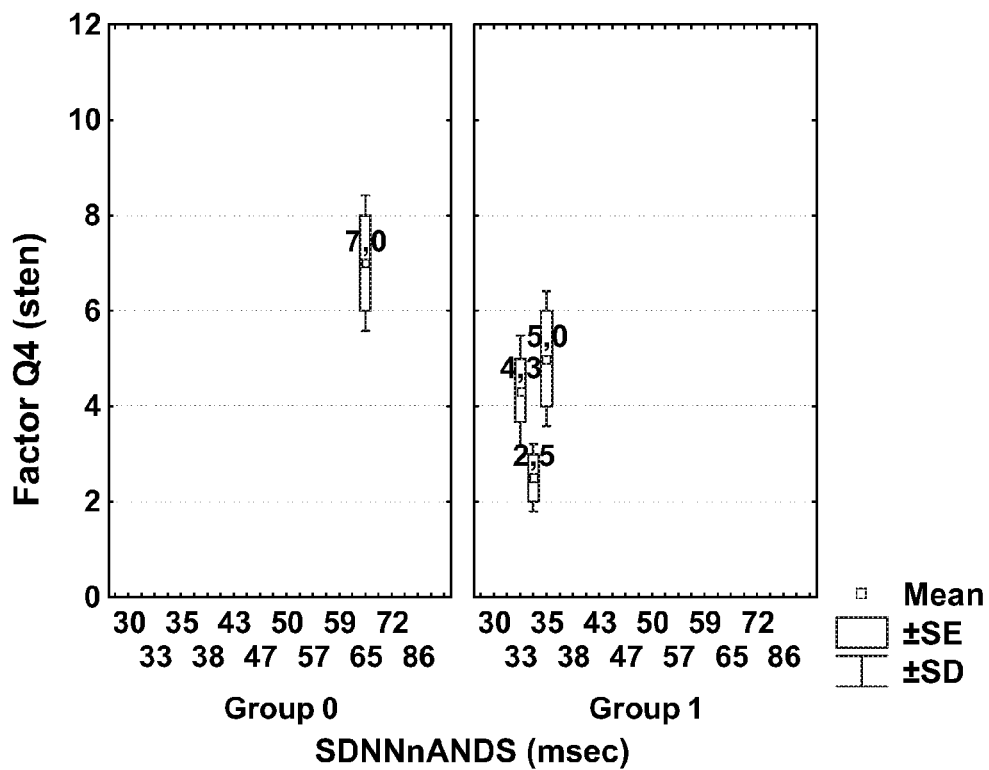

Statistically significant index of the night hypersympathicotonia syndrome, that predestined the morning differences of the characteristics in accordance with the R. B. Cattell technique have been the indices SDNNnANDS, pNN50% nANDS, TInANDS and INnANDS. In comparison with the control group (hereinafter, GR. 0), the more expressed nighttime decrease of the index SDNNnANDS predestined a relative decrease of the factor I and factor Q4 in the next morning (see. FIGS. 9, 10), the similar decrease of the index pNN50% nANDS predestined a decrease of the factor I and factor A (see FIGS. 11, 12), and a decrease of the index TInANDS predestined a decrease of the factors A, C, F, I (see FIGS. 13, 14, 15, 16, respectively).

Relatively to GR. 0, a significant increase of the value INnANDS (increase of the index of intension of the vegetative regulation according to R. M. Baevsky in the presence of the night hypersympathicotonia syndrome) resulted in decrease of the factors F and Q3 (see FIGS. 17, 18).

The identified significant tendency for the single-type reduction of all adduced characteristics of the R. B. Cattell technique on the next morning permitted for considering those changes as the single-type, where the factors A and F reflected a relative deterioration of the communicative sphere of personality of patients from the GR. 1, and the factors C, I, Q3, Q4 reflected a relative regression of the emotional-volitional sphere.

In addition to that, when considering the factor combinations grouped under each of the hypersympathicotonia indices, it could be concluded that the index pNN50% nANDS grouped the decrease both the communicative sphere (factor A), and the emotional sphere (factor I) of patients from the GR. 1. The similar changes in the form of combination of the characteristics of the emotional-volitional and communicative sphere reduced in the GR. 1 related to the indices TInANDS and INnANDS (see the Table 2), which does not permit to consider separately the manifestations of deteriorations in the communicative and emotional-volitional sphere in the GR. 1.

Consideration of changes of every significant characteristic separately has permitted to conclude that the night hypersympathicotonia in the GR. 1 predestined a comparative reduction of the factor A, which signifies the more expressed manifestation of the "schizothymia" or, correspondingly, the predominance of reticence, isolation, estrangement, asociality.

A reliable reduction of the factor C and factor I relative to the control GR. 0 characterizes emotional-volitional particularities of the psychological functioning and signifies for the factor C the more expressed "Lower Ego Strength" signifying foible, emotionally less stable, impulsivity, when a patient affected by feelings, changeable in tempers, easily upset, changeable in interests, has a low tolerance to frustration, irritancy, fatigability.

A relative reduction of the factor I for the GR. 1 indicated a manifestation of "Harria", i.e., a relatively lower sensitivity, presence of deliberativeness, realism, some rough, severity, obduracy in relationships, which all are predestinated by the night hypersympathicotonia.

A relative reliable reduction of the factor F signified an intensification of "desurgency, demureness", where a more expressed reticence, taciturnity, preoccupation, caution in selecting a company, anxiety for future, pessimism in reality perception. A relative and unfeatured reduction of the factor Q3 in the GR. 1 predestined by the night hypersympathicotonia signified manifestations of the "lower self-opinion" and, respectively, inattention and indelicacy, indiscipline, interior conflict proneness of self-conceptions.

A relative lower values of the factor Q4 in the GR. 1 indicated onto manifestations of "low ego-tension" observed in the form of relatively greater languor, demureness, low motivation.

Statistically significant index of the night hypersympathicotonia syndrome, that predestined the morning differences of the characteristics in accordance with the technique "Secondary factors" have been the indices RMSSDnANDS, pNN50% nANDS, TInANDS. Relative to the GR>1, the more expressed nighttime reduction of the indices RMSSDnANDS and TInANDS predestined a relative reduction of the factor F2 in the next morning (see FIGS. 19, 21), and a similar relative reduction of the index pNN50% nANDS predestined an increase of the value of the factor F3 (FIG. 20).

Thus, the interpretation of the obtained data was resolved to a relative reduction of the factor F2 and, at the same time, to the increase of the factor F3. A relative reduction of the value of the factor F2 characterizes a dominance of the introversion and, respectively, signifies a relative dominance of such properties in the GR. 1 as demureness, reticence, being repressed in interpersonal conflicts. A relative increase of the value of the factor F3 indicated the intensification of "reactive tranquility" characterized by predisposition for not to notice life details, awareness onto some evident, obvious. Patients of the GR. 1 undergo hardship because of too hasty actions without sufficient weighing.

As could be seen, the results of the performed psychological testing confirm distinctly the relationship between the presence of the night hypersympathicotonia syndrome objectively determined and unfavorable human emotional-behavioral states and psychophysiological functioning While the present invention has been described herein by means of the specific embodiment, this description has only illustrative rather than the limiting character. The scope of this invention is defined not by this description, but by the enclosed claims enclosing all possible modifications of the present invention taking into account the equivalents.

Figure 2:
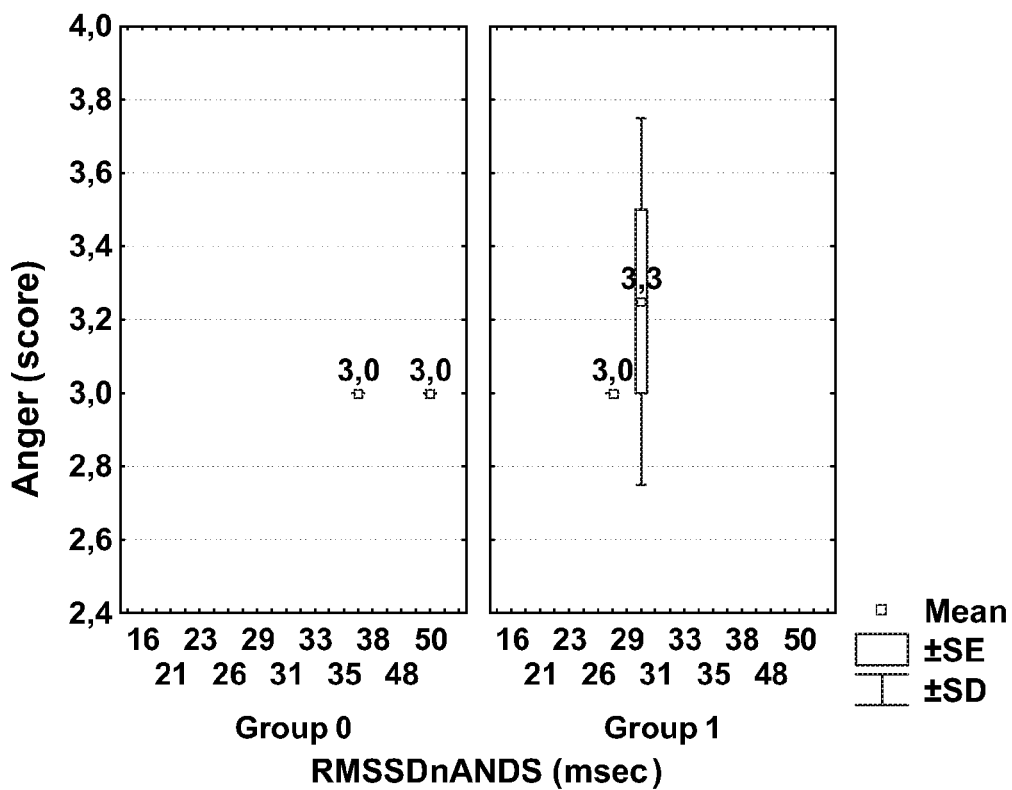
Figure 3:
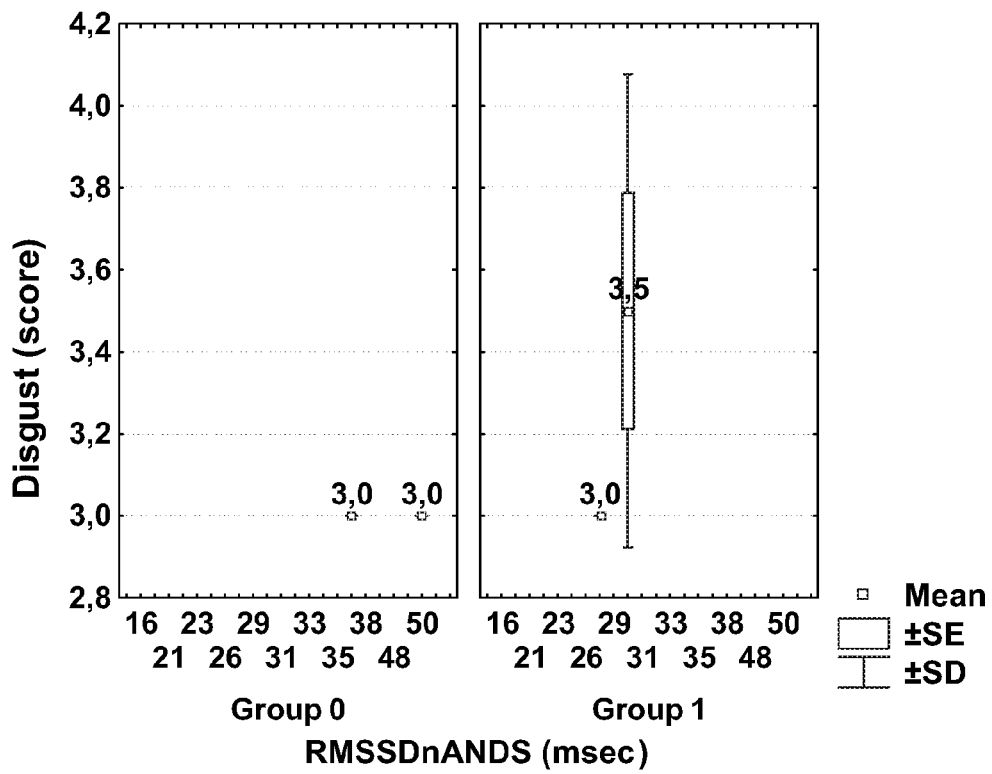
Figure 4:
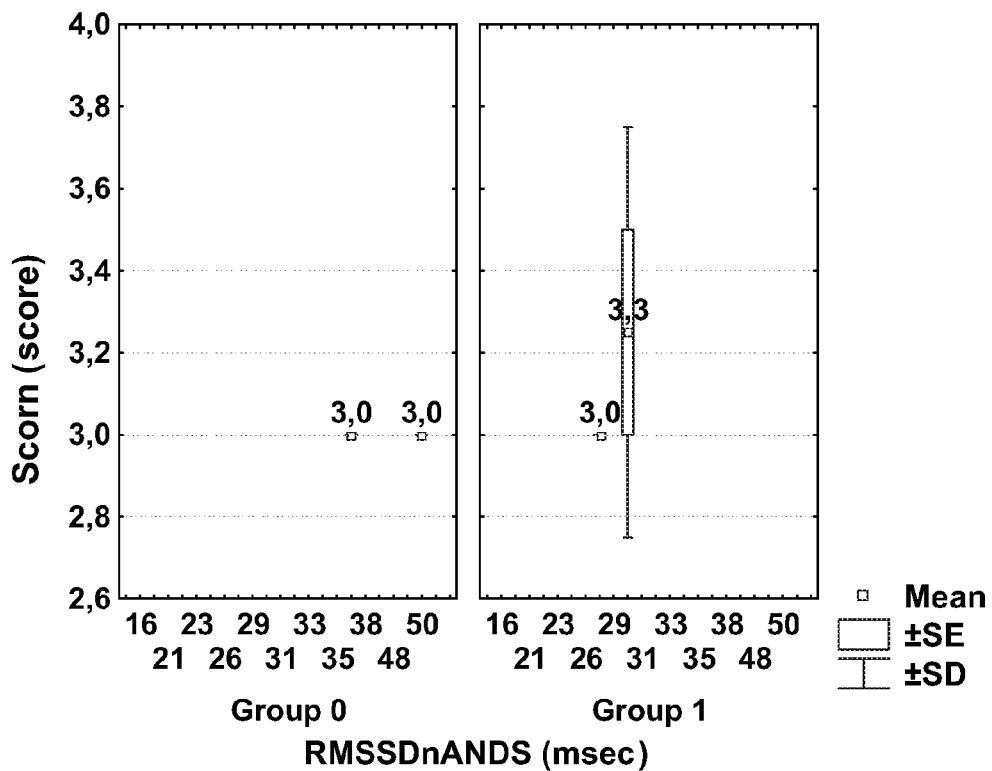
Figure 5:
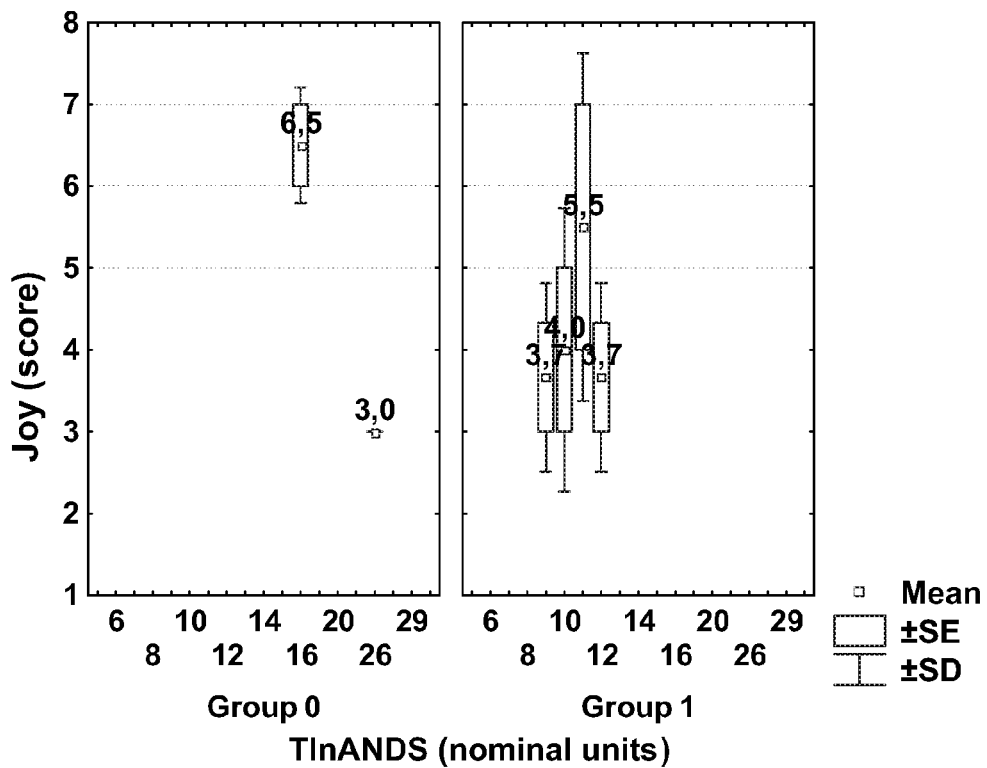
Figure 6:
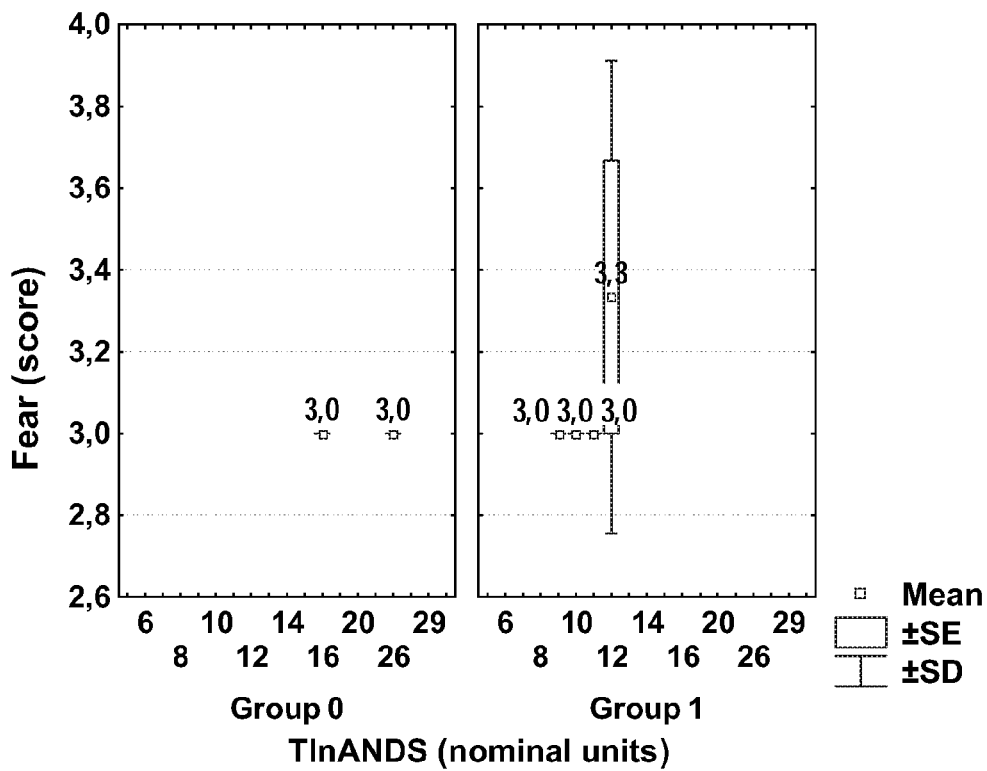

| Inscriptions in the Drawings | |
|---|---|
| FIG.1: | |
| (left) - Anger (score) | |
| (bottom) - Group 0 | Group 1 |
| pNN50%nANDS (in percentage terms) | |
| FIG.2: | |
| (left) - Anger (score) | |
| (bottom) - Group 0 | Group 1 |
| RMSSDnANDS (msec) | |
| FIG.3: | |
| (left) - Disgust (score) | |
| (bottom) - Group 0 | Group 1 |
| RMSSDnANDS (msec) | |
| FIG.4: | |
| (left) - Scorn (score) | |
| (bottom) - Group 0 | Group 1 |
| RMSSDnANDS (msec) | |
| FIG.5: | |
| (left) - Joy (score) | |
| (bottom) - Group 0 | Group 1 |
| TinANDS (nominal units) | |
| FIG.6: | |
| (left) - Fear (score) | |
| (bottom) - Group 0 | Group 1 |
| TinANDS (nominal units) | |
| FIG.7: | |
| (left) - Compensation (score) | |
| (bottom) - Group 0 | Group 1 |
| pNN50%nANDS (in percentage terms) | |

Figure 8:
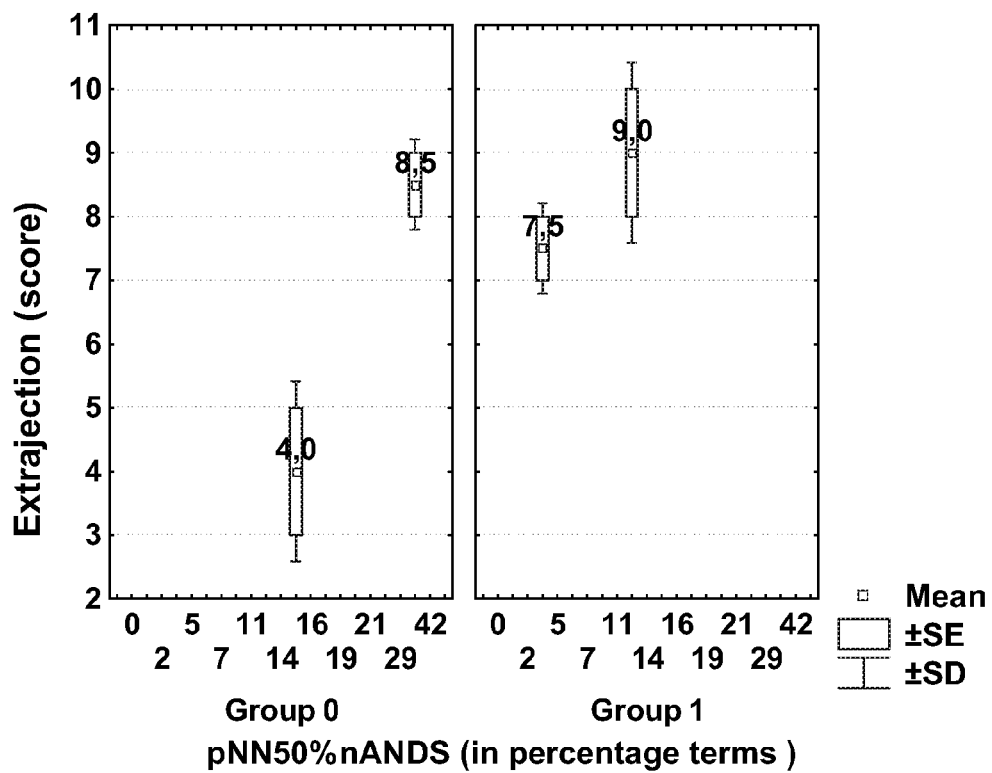
Figure 11:
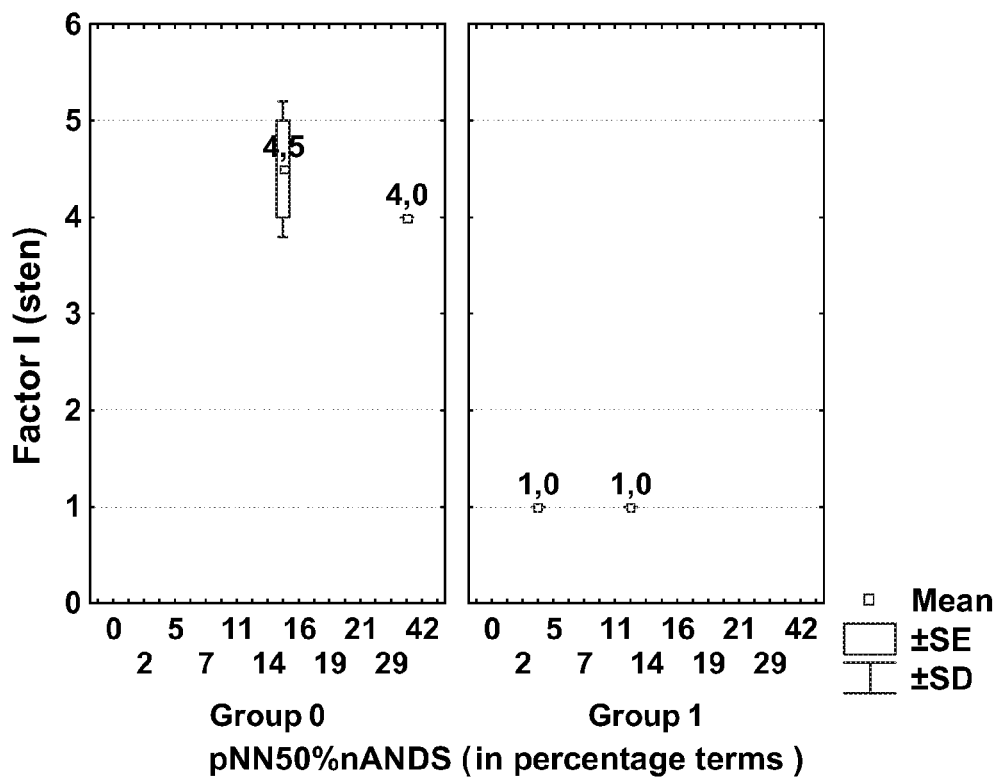
Figure 12:
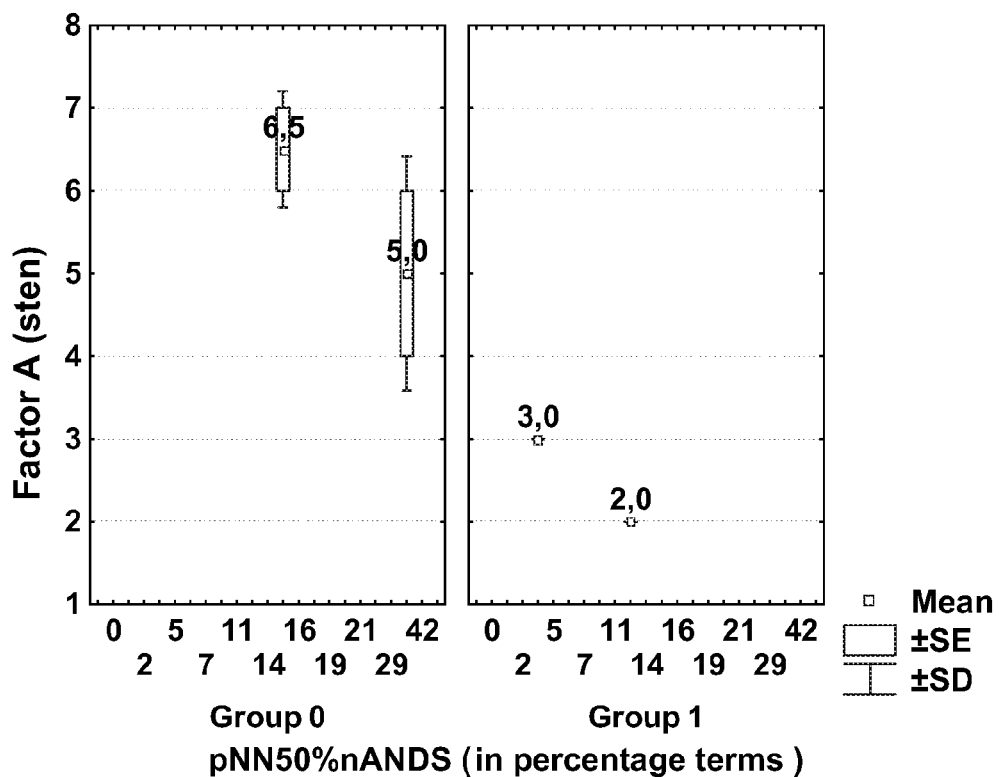
Figure 13:
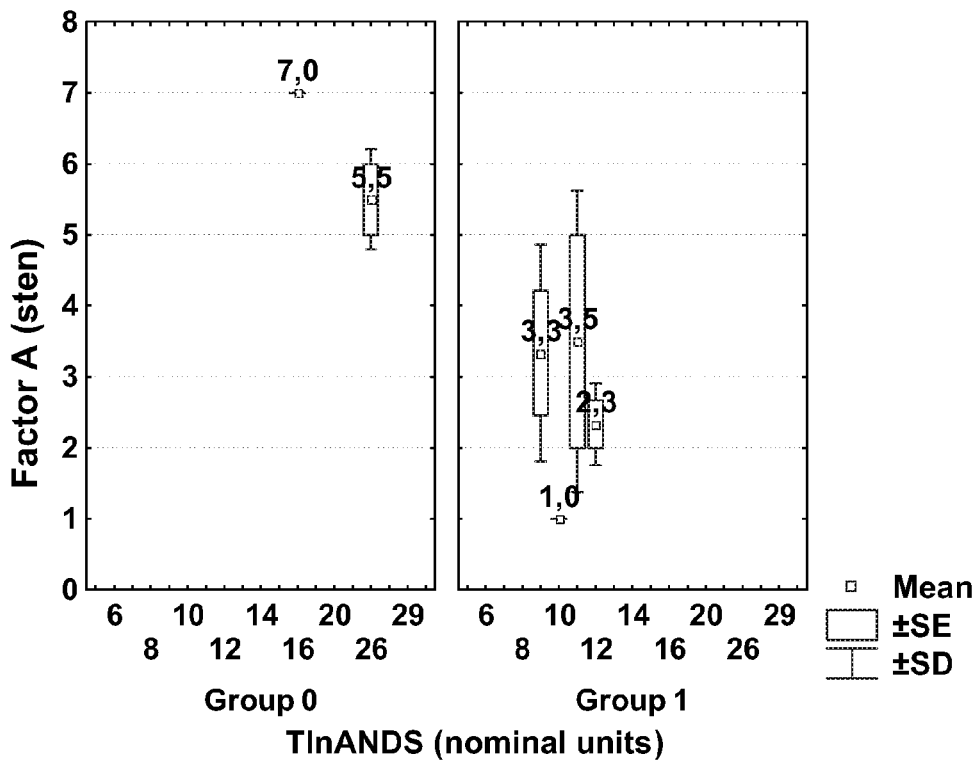
Figure 14:
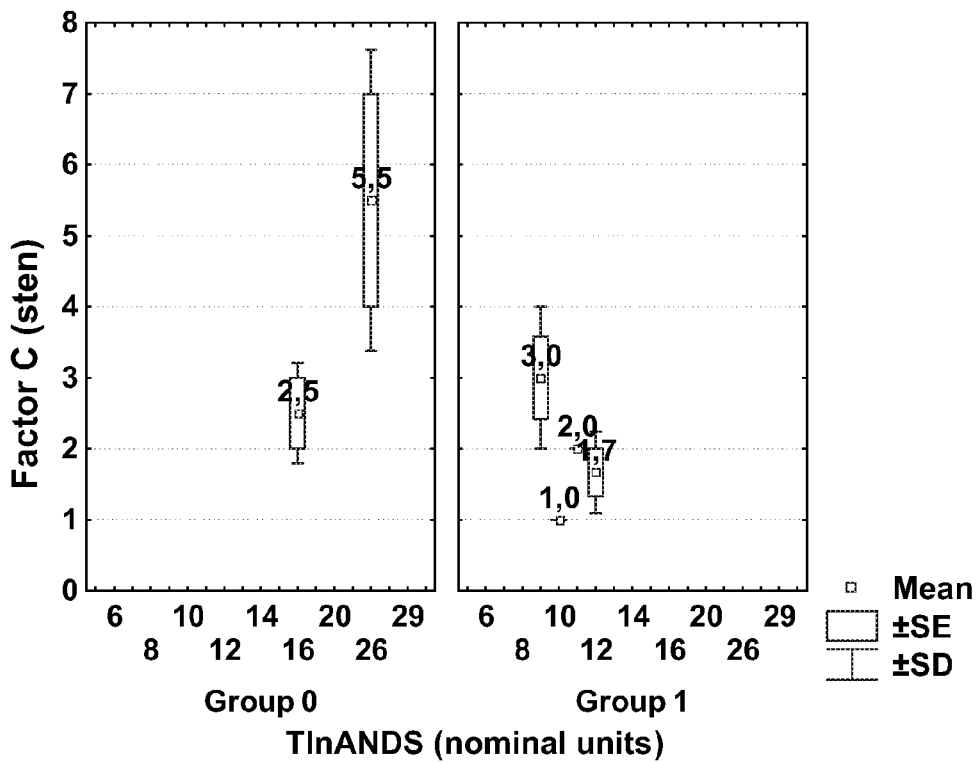
Figure 15:
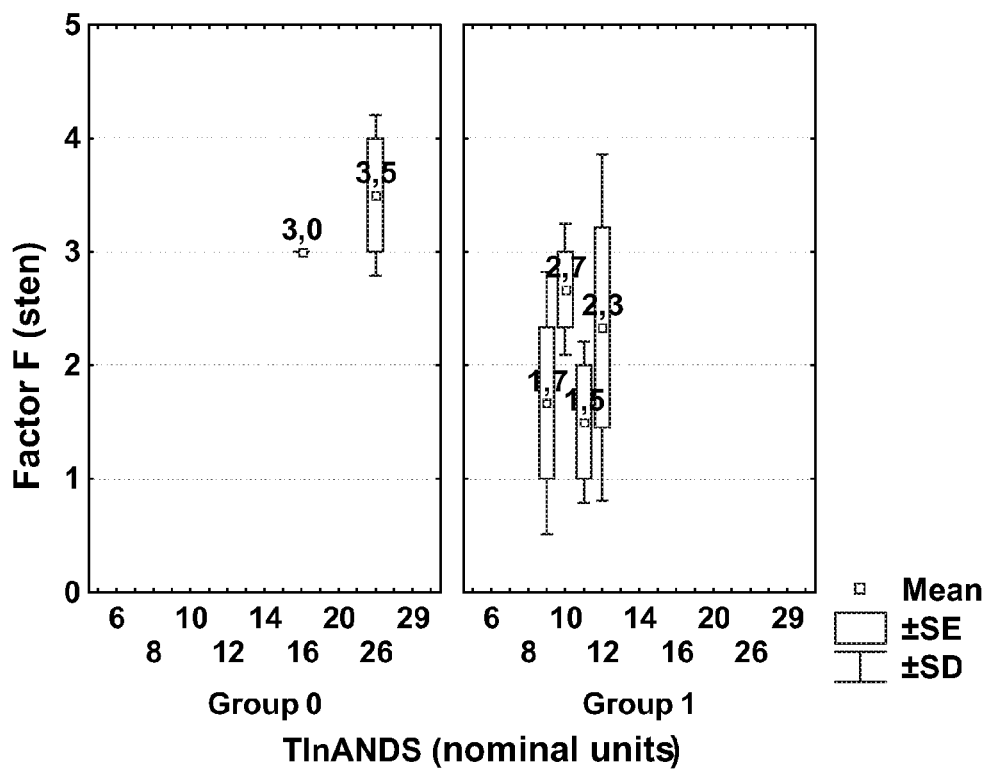
Figure 16:
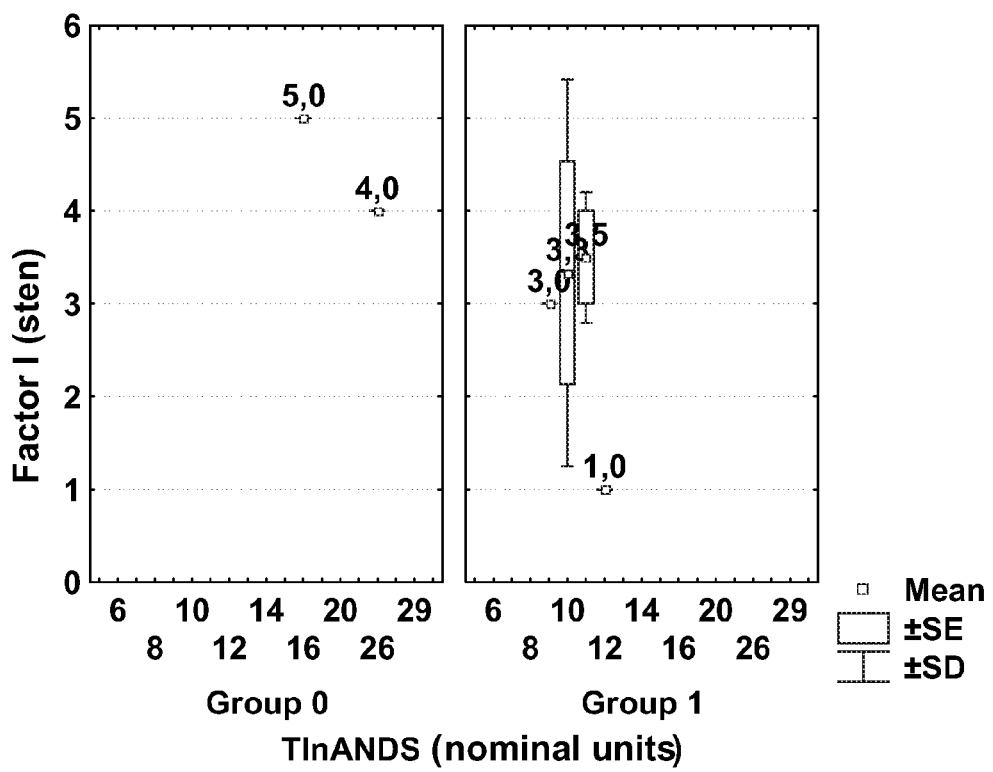
Figure 17:
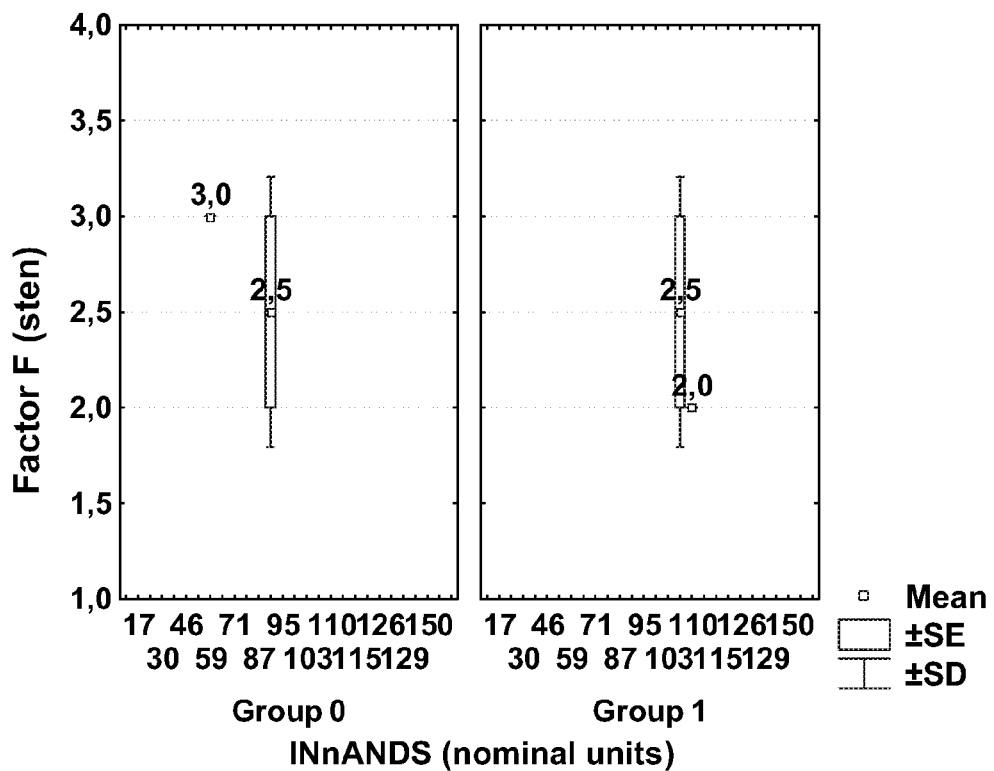
Figure 18:
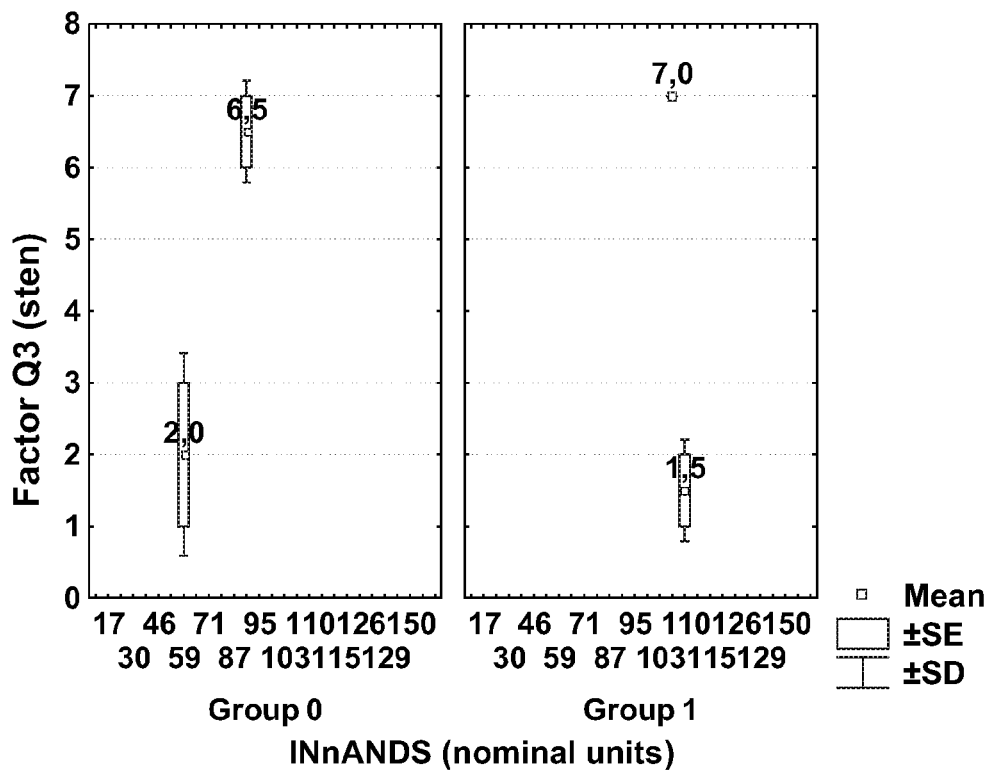
Figure 19:
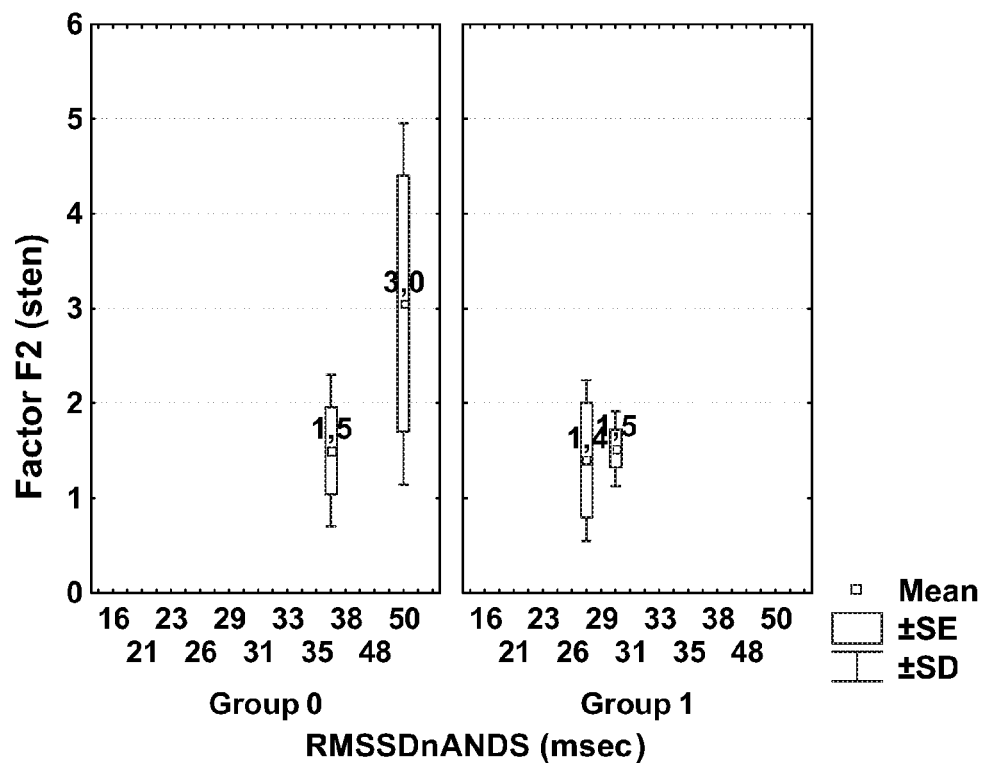
FIGS. 19 to 21 show the diagrams of various daytime indices obtained in accordance with the R. B. Cattell technique for the secondary factors along with classification by one of the night hypersympathicotonia syndrome indices.
Figure 20:
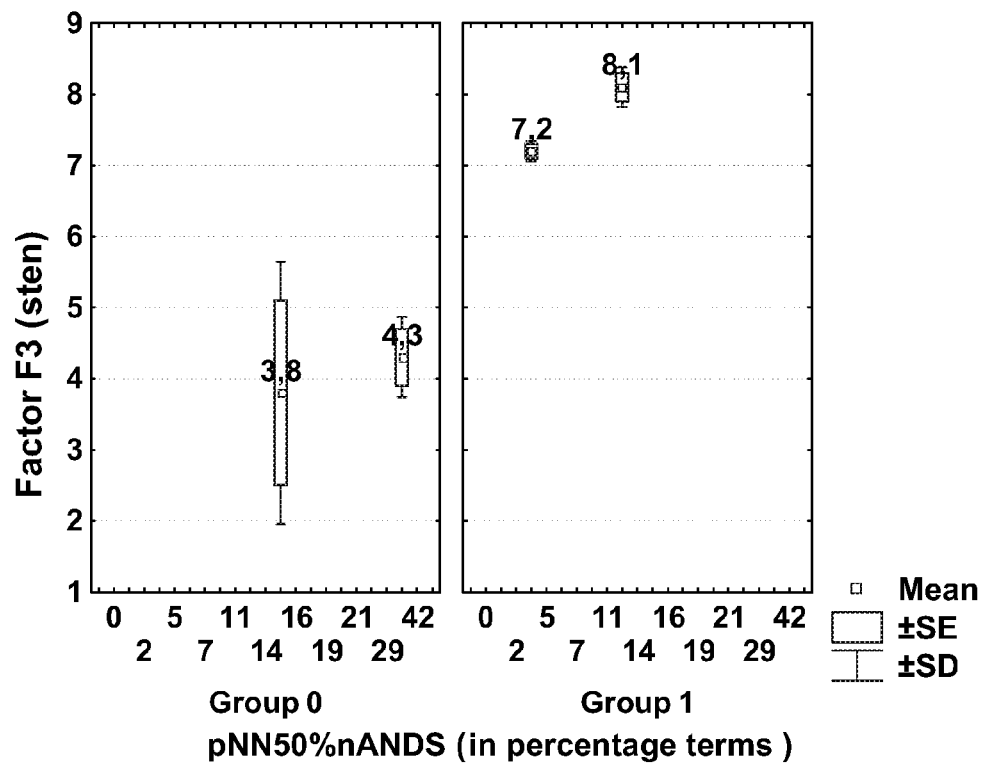
Figure 21:
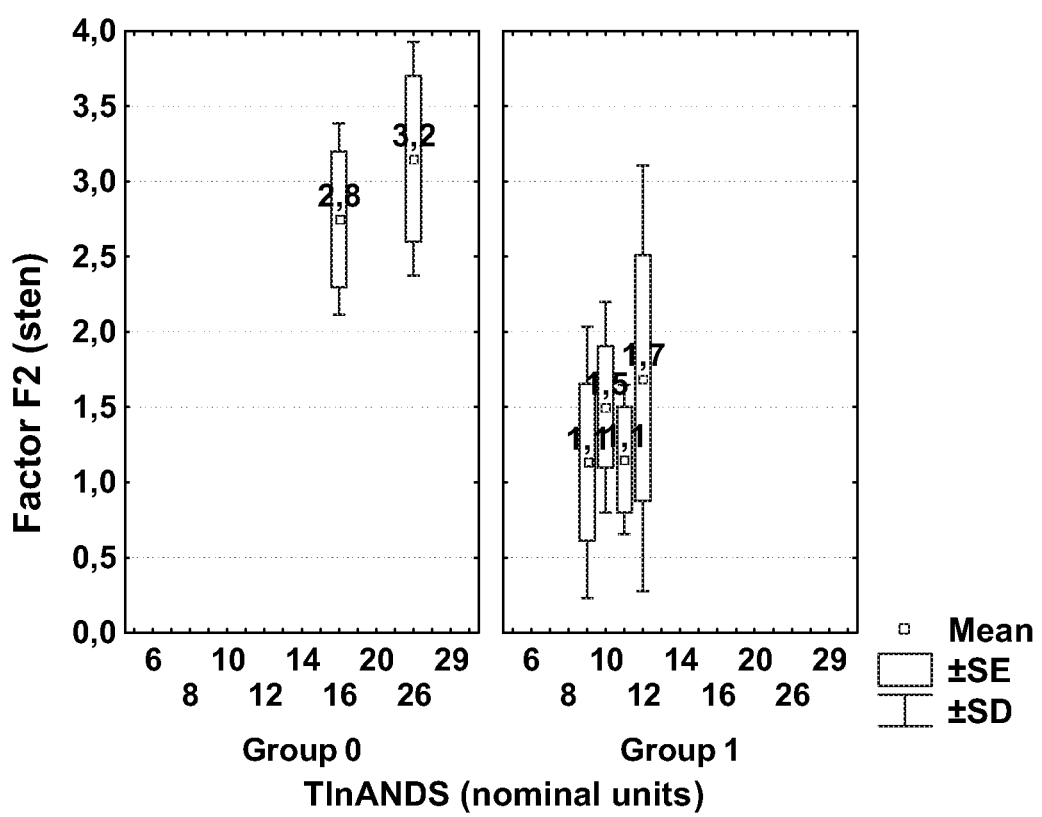

| Inscriptions in the Drawings |
|---|
| FIG.8:  |
| (left) - Extrajection (score) |
| (bottom) - Group 0    Group 1 |
| pNN50%nANDS (in percentage terms) |
| FIG.9: |
| (left) - Factor I (sten) |
| (bottom) - Group 0    Group 1 |
| SDNNnANDS (msec) |
| FIG.10: |
| (left) - Factor Q4 (sten) |
| (bottom) - Group 0    Group 1 |
| SDNNnANDS (msec) |
| FIG.11: |
| (left) - Factor I (sten) |
| (bottom) - Group 0    Group 1 |
| pNN50%nANDS (in percentage terms) |
| FIG.12: |
| (left) - Factor A (sten) |
| (bottom) - Group 0    Group 1 |
| pNN50%nANDS (in percentage terms) |
| FIG.13: |
| (left) - Factor A (sten) |
| (bottom) - Group 0    Group 1 |
| TinANDS (nominal units) |
| FIG.14: |
| (left) - Factor C (sten) |
| (bottom) - Group 0    Group 1 |
| TinANDS (nominal units) |
| FIG.15: |
| (left) - Factor F (sten) |
| (bottom) - Group 0    Group 1 |
| TinANDS (nominal units) |
| FIG.16: |
| (left) - Factor I (sten) |
| (bottom) - Group 0    Group 1 |
| TinANDS (nominal units) |
| FIG.17: |
| (left) - Factor F (sten) |
| (bottom) - Group 0    Group 1 |
| INnANDS (nominal units) |
| FIG.18: |
| (left) - Factor Q3 (sten) |
| (bottom) - Group 0    Group 1 |
| INnANDS (nominal units) |
| FIG.19: |
| (left) - Factor F2 (sten) |
| (bottom) - Group 0    Group 1 |
| RMSSDnANDS (msec) |
| FIG.20: |
| (left) - Factor F3 (sten) |
| (bottom) - Group 0    Group 1 |
| pNN50%nANDS (in percentage terms) |
| FIG.21: |
| (left) - Factor F2 (sten) |
| (bottom) - Group 0    Group 1 |
| TinANDS (nominal units) |
| FIG.22,24-26,28: |
| (above the intervalogram) - |
| Record analysis of the RR intervals |
| of . . . over the period of . . . |
| Dynamics of the RR intervals (Var) |
| (at the bottom left corner of the |
| intervalogram) - msec/hour |
| (beneath the intervalogram, in row) - |
| Whole period 1st period 2nd period |
| (left, in column) -    Interval, hours:minutes |
|                        Extrasystoles |
|                        Correction, % |
|                        NN, msec |
|                        SDNN, msec |
|                        SDANN, msec |
|                        RMSSD, msec |
|                        pNN50, % |
|                        TI |
|                        VLFp, msec$^2$ |
|                        LFp, msec$^2$ |
|                        HFp, msec$^2$ |
|                        LF/HF |
|                        Baevsky index (BI) |
| (right, in column) -   Print |
|                        Export |
|                        Statistics |
|                        Spectrum |
|                        by Baevsky |
|                        Close |
| FIG.23,27,29: |
| (above the intervalogram) - |
| Record analysis of the RR intervals |
| of . . . over the period of . . . |
| Baevsky index (BI) |
| (at the bottom left corner of the |
| intervalogram) - msec/hour |
| (beneath the intervalogram, in row) - Whole period 1st period 2nd period |
| (left, in column) -    Interval, hours:minutes |
|                        Extrasystoles |
|                        Correction, % |
|                        NN, msec |
|                        SDNN, msec |
|                        SDANN, msec |
|                        RMSSD, msec |
|                        pNN50, % |
|                        TI |
|                        VLFp, msec$^2$ |
|                        LFp, msec$^2$ |
|                        HFp, msec$^2$ |
|                        LF/HF |
|                        Baevsky index (BI) |
| (right, in column) -   Print |
|                        Export |
|                        Statistics |
|                        Spectrum |
|                        by Baevsky |
|                        Close |

The invention claimed is:

1. A method for predicting human emotional states and psychophysiological functioning by measuring indices of night hypersympathicotonia syndrome, the method comprising steps of:

a) monitoring a patient's ECG using an ECG device for a period of at least approximately 24 hours and recording the patient's ECG data;

b) entering and storing the patient's ECG data in computer memory;

c) constructing an intervalogram using a computer processor and using the patient's ECG data, and storing the intervalogram in computer memory;

d) selecting using a computer a night time span in the intervalogram corresponding to nighttime, and selecting using a computer a day time span in the intervalogram corresponding to daytime, wherein both time spans have an equal duration, the durations being not less than 30 minutes;

e) comparing cardiac rhythm variability of the day time span and of the night time span and determining a patient cardiac variability profile comprising that comparison;

f) providing a comparison set in computer memory, the comparison set comprising physiological data indicative of a presence or absence of night hypersympathicotonia syndrome, including daytime and nighttime cardiac rhythm variability data, for a plurality of comparison individuals, some of whom have night hypersympathicotonia syndrome and some of whom do not have night hypersympathicotonia syndrome, the comparison set also including psychological characteristics for the comparison individuals determined using psychological testing; and g) comparing the patient cardiac variability profile and the comparison set, and predicting the patient's psychological characteristics based on the physiological and psychological characteristics of the comparison individuals contained in the comparison set.

2. The method of claim 1, wherein the comparison set is created ahead of time by a process comprising monitoring and recording the comparison individuals' ECG for a period of at least approximately 24 hours, and performing psychological testing of each comparison individual after their ECG monitoring ends.

3. The method of claim 2, further comprising creating an intervalogram for each comparison individual.

4. The method of claim 3, the process for creating the comparison set further comprising selecting a night time span in each comparison individual intervalogram corresponding to nighttime, and selecting a day time span in each comparison individual intervalogram corresponding to daytime, wherein both time spans have an equal duration, the duration being not less than 30 minutes;

for each comparison individual intervalogram, comparing the cardiac rhythm variability of the day time span and the cardiac rhythm variability night time span to determine a cardiac variability ratio;

correlating the cardiac variability ratios for the plurality of comparison individuals with the psychological characteristics of the plurality of comparison individuals and including said correlations in the comparison set.

5. The method of claim 4, wherein the comparison set comprises separate cardiac variability ratio data for comparison individuals who have and who do not have night hypersympathicotonia syndrome.

6. The method of claim 4, wherein the day time spans and night time spans for the comparison individuals have the same duration as the day time span and the night time span for the patient.

7. The method of claim 1, wherein the cardiac rhythm variability of the patient is plotted in a graph.

8. The method of claim 1, wherein the comparison set comprises a first table comprising comparisons of physiological data for test individuals having night hypersympathicotonia syndrome with physiological data for test individuals who do not have night hypersympathicotonia syndrome; and wherein the comparison set comprises a second table comprising comparisons of physiological data for test individuals with psychological testing results for the test individuals.

9. The method of claim 4, wherein the comparison set comprises a first table comprising comparisons of physiological data for test individuals having night hypersympathicotonia syndrome with physiological data for test individuals who do not have night hypersympathicotonia syndrome;

wherein the comparison set comprises a second table comprising comparisons of physiological data for test individuals with psychological testing results for the test individuals; and wherein the physiological data comprises cardiac variability ratios.

* * * * *